(12) United States Patent
Watanabe et al.

(10) Patent No.: US 7,400,396 B2
(45) Date of Patent: Jul. 15, 2008

(54) FLUORESCENT CORREALATED SPECTROMETRIC ANALYSIS DEVICE

(75) Inventors: Hirohiko Watanabe, Shizuoka (JP); Motoyuki Watanabe, Shizuoka (JP); Takayuki Inoue, Shizuoka (JP); Tadashi Maruno, Shizuoka (JP); Fumio Iwase, Shizuoka (JP)

(73) Assignee: Hamanatsu Photonics K.K., Shizuoka (JP)

( * ) Notice: Subject to any disclaimer, the term of this patent is extended or adjusted under 35 U.S.C. 154(b) by 76 days.

(21) Appl. No.: 10/545,393

(22) PCT Filed: Feb. 13, 2004

(86) PCT No.: PCT/JP2004/001558

§ 371 (c)(1),
(2), (4) Date: May 23, 2006

(87) PCT Pub. No.: WO2004/072624

PCT Pub. Date: Aug. 26, 2004

(65) Prior Publication Data

US 2006/0262301 A1     Nov. 23, 2006

(30) Foreign Application Priority Data

Feb. 13, 2003   (JP) ............................. 2003-035415
Oct. 10, 2003   (JP) ............................. 2003-352638

(51) Int. Cl.
*G01J 3/30*   (2006.01)
(52) U.S. Cl. ..................................... 356/317
(58) Field of Classification Search ........................ None
See application file for complete search history.

(56) References Cited

U.S. PATENT DOCUMENTS

| 5,233,197 A | 8/1993 | Bowman et al. |
| 6,582,903 B1 | 6/2003 | Rigler et al. |
| 6,798,509 B2 * | 9/2004 | Sonehara et al. ............ 356/344 |

FOREIGN PATENT DOCUMENTS

| EP | 1 122 534 | 8/2001 |
| EP | 1 174 706 | 1/2002 |
| JP | 10-191176 | 7/1998 |
| JP | 11-46323 | 2/1999 |
| JP | 11-191863 | 7/1999 |
| JP | 2000-166598 | 6/2000 |
| JP | 2001-194303 | 7/2001 |

(Continued)

*Primary Examiner*—Tu T Nguyen
(74) *Attorney, Agent, or Firm*—Drinker Biddle & Reath LLP

(57) ABSTRACT

A fluorescence correlation spectroscopy analyzer 1 is equipped with an excitation light illuminating optical system 21, a fluorescence imaging optical system 22, a CCD camera 15, and a data analyzer 16. The excitation light illuminating optical system 21 illuminates excitation light onto a predetermined region of a measured sample S. The fluorescence imaging optical system 22 images the fluorescence generated at the measured sample S onto the photodetection surface of the CCD camera 15. The CCD camera 15 performs photoelectric conversion of the fluorescence made incident onto the photodetection surface in accordance with the respective pixels and outputs the charges generated by the photoelectric conversion as detection signals from an output terminal. The data analyzer 16 inputs the detection signals based on the charges generated at the pixels, and computes autocorrelation functions of the input detection signals according to each pixel.

9 Claims, 18 Drawing Sheets

FOREIGN PATENT DOCUMENTS

| | | |
|---|---|---|
| JP | 2001-194305 | 7/2001 |
| JP | 2001-212072 | 8/2001 |
| JP | 2001-212073 | 8/2001 |
| JP | 2001-272346 | 10/2001 |
| WO | WO 99/23474 | 5/1999 |

* cited by examiner

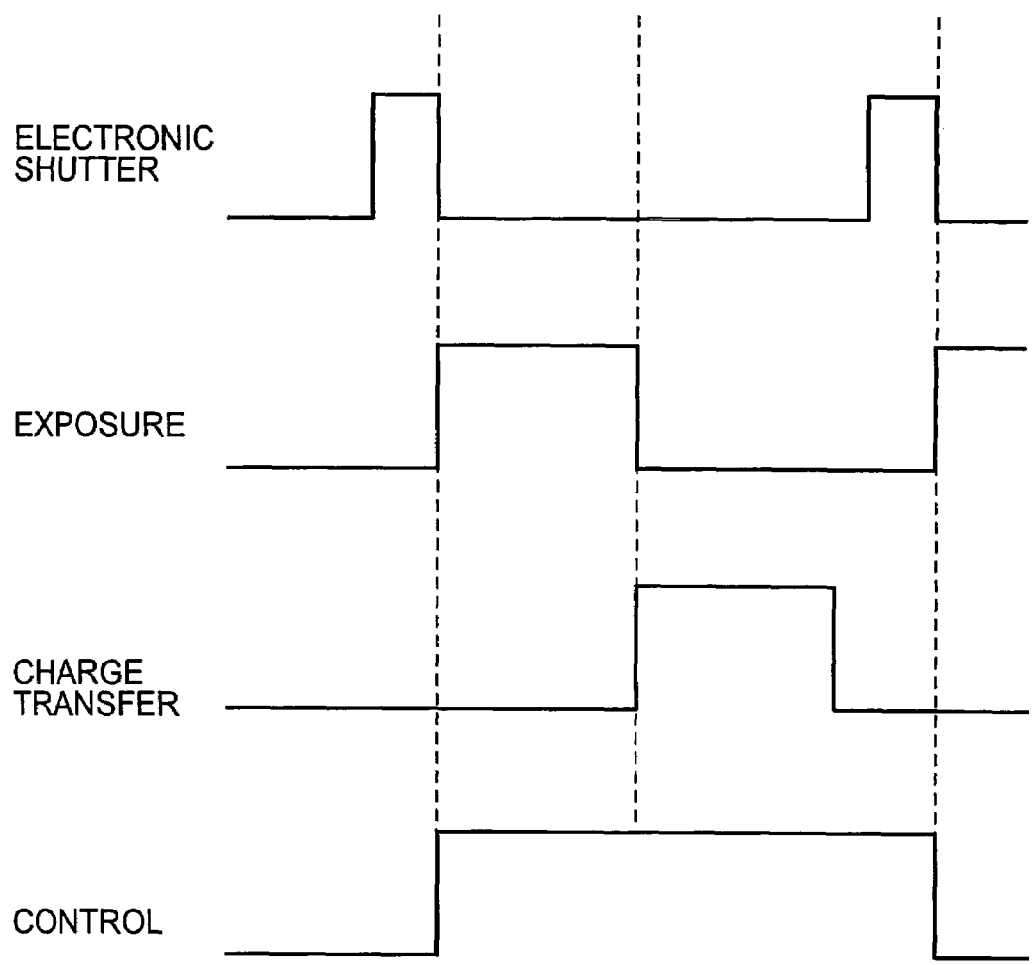

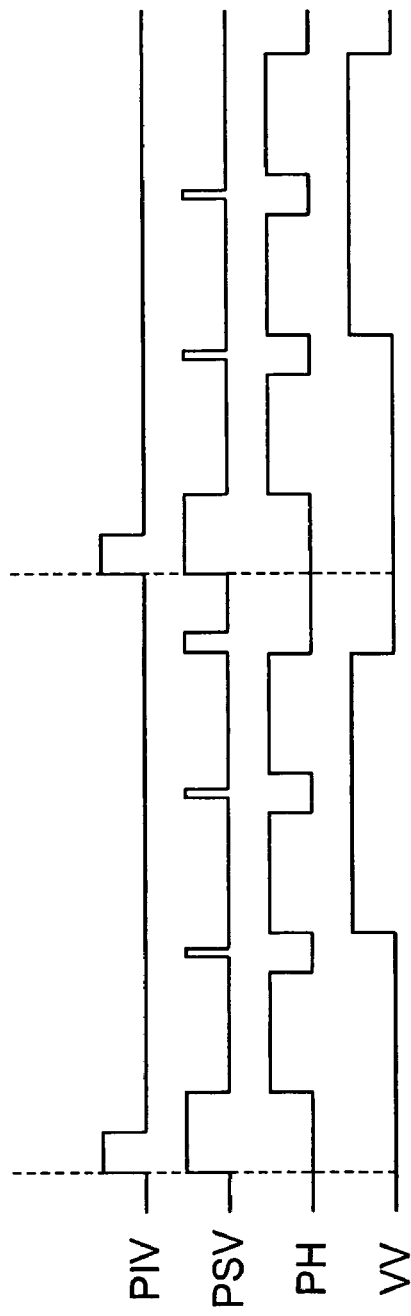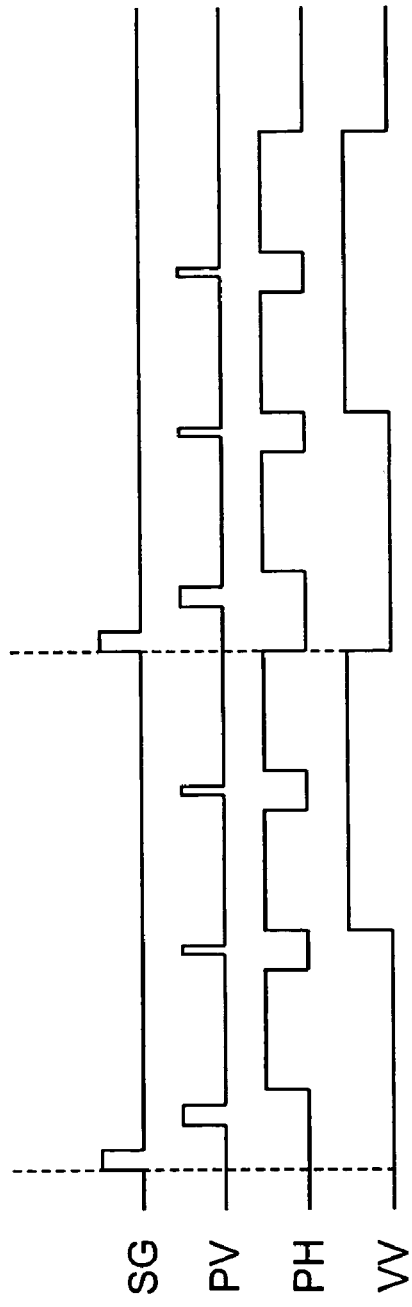

FLUORESCENT CORREALATED SPECTROMETRIC ANALYSIS DEVICE

TECHNICAL FIELD

The present invention relates to a fluorescence correlation spectroscopy analyzer.

BACKGROUND ART

Fluorescence correlation spectroscopy (FCS) is a method wherein the fluorescence fluctuations (variations of the fluorescence intensity in time) of fluorescent molecules in a measured sample are measured and autocorrelation functions are determined from the fluorescence fluctuations to analyze the translational diffusion motions, etc., of the fluorescent molecules. By FCS, for example, the binding and motion of a single protein molecule can be analyzed.

Examples of conventional analyzers that make use of FCS include those described in Document 1 (Japanese Patent Application Laid-Open No. 2000-166598), Document 2 (Japanese Patent Application Laid-Open No. 2001-272346), and Document 3 (Japanese Patent Application Laid-Open No. 2001-194305). With the analyzer described in Document 1, a point-like excitation light is illuminated onto a single point of a measured sample and the fluorescence emitted from the measured sample is detected by a detector, such as a photomultiplier tube (PMT) or an avalanche photodiode (APD). With the analyzer described in Document 2, pulse excitation light is illuminated onto a measured sample while scanning and the fluorescence from the measured sample is detected by a CCD camera.

DISCLOSURE OF THE INVENTION

With the analyzer described in Document 1, since the excitation light is illuminated onto just one point of the measured sample, a plurality of points of the measured sample cannot be analyzed simultaneously. Movement of a substance within a cell thus cannot be measured.

On the other hand, with the analyzer described in Document 2, by the use of the CCD camera as the detector, simultaneous analysis of a plurality of points of a measured sample is enabled. However, when a CCD camera is used, since the detection signals of the respective pixels must be read out in order one by one, a large amount of time is required to read out the detection signals of a single frame. Thus, with the analyzer described in Document 2, detection signals cannot be read out at a high speed, for example, in the order of μs. Thus, an analyzer, capable of performing fluorescence correlation spectroscopy analysis of fluorescent molecules at multiple points within a micro-time domain of the μs level, etc., did not exist.

The present invention has been made to resolve the above issues and an object thereof is to provide a fluorescence correlation spectroscopy analyzer that enables fluorescence correlation spectroscopy analysis to be performed simultaneously on multiple points of a measured sample at high speed.

In order to resolve the above issues, the present invention's fluorescence correlation spectroscopy analyzer comprises: an excitation light illuminating optical system, illuminating excitation light onto a predetermined region of a measured sample; a fluorescence imaging optical system, imaging the fluorescence emitted from fluorescent molecules within the predetermined region of the measured sample onto which the excitation light has been illuminated from the excitation light illuminating optical system; a detector, having a photodetection surface, disposed on an image plane position of the fluorescence imaged by the fluorescence imaging optical system and provided with a plurality of pixels that are arrayed two-dimensionally along a first direction and a second direction that intersect mutually, photoelectrically converting, according to the respective pixels, the fluorescence made incident on the photodetection surface, transferring the charges generated by the photoelectrical conversion in the first direction and the second direction, and outputting the charges as detection signals from an output terminal; and an analyzing unit, inputting the detection signals from pixels belonging to a pixel set, comprising a portion of pixels selected from among all of the pixels, arrayed on the photodetection surface, in accordance with the incidence region of the photodetection surface on which the fluorescence is imaged by the fluorescence imaging optical system, and determining an autocorrelation function for each of the detection signals.

With this fluorescence correlation spectroscopy analyzer, excitation light is illuminated onto the predetermined region of the measured sample by the excitation light illuminating optical system. The fluorescence emitted from the fluorescent molecules in the predetermined region of the measured sample onto which the excitation light has been illuminated is then imaged on the photodetection surface of the detector by the fluorescence imaging optical system. The fluorescence made incident on the photodetection surface is then photoelectrically converted according to the respective pixels. The charges generated at the respective pixels by the photoelectric conversion are output as detection signals from the output terminal of the detector. The detection signals output from the detector are input into the analyzing unit. At the analyzing unit, the autocorrelation functions of the detection signals are determined.

Thus, with this fluorescence correlation spectroscopy analyzer, the fluorescence, emitted from multiple points within the region of the measured sample onto which the excitation light has been illuminated, is detected by the plurality of pixels of the detector that correspond to these points to enable fluorescence correlation spectroscopy analysis of the multiple points of the measured sample to be performed simultaneously. Also, by the use of a charge transfer type two-dimensional photodetector as the detector, the fluorescence generated at multiple points of the measured sample can be detected by a simple device arrangement.

Furthermore, the analyzing unit determines the autocorrelation functions of the detection signals based on the charges generated at the pixels belonging to the pixel set that is comprised of a portion of the pixels of the entirety of pixels arrayed on the photodetection surface. Thus, with the detector, the charges generated at all of the pixels of the photodetection surface do not need to be output as effective detection signals, and it is sufficient that at least the pixels belonging to the pixel set be output as the detection signals. Thus, with this fluorescence correlation spectroscopy analyzer, the time required for outputting the charges of a single frame from the detector can be shortened. Fluorescence correlation spectroscopy analysis can thus be performed at high speed on multiple points of a measured sample with this fluorescence correlation spectroscopy analyzer.

Preferably on the photodetection surface, the pixels in the fluorescence incidence region substantially match the pixels belonging to the pixel set. In this case, at the analyzing unit, the autocorrelation functions are determined for the detection signals based on the charges generated at the pixels onto which the fluorescence, generated at the predetermined region of the measured sample illuminated by the excitation light, is made incident. Both the fluorescence made incident on the photodetection surface of the detector and the excitation light illuminated onto the measured sample are thereby used effectively in fluorescence correlation spectroscopy analysis.

Preferably, a scanning means is equipped by which the excitation light, illuminated by the excitation light illuminating optical system onto the predetermined region of the measured sample, is scanned with respect to the measured sample. In this case, fluorescence correlation spectroscopy analysis can be performed on a wide range of the measured sample.

Preferably, the scanning means is a galvanomirror. In this case, the excitation light can be scanned with respect to the measured sample at an especially high precision.

Preferably, the detector has a horizontal transfer register, which receives and accumulates the charges that are transferred in the first direction from the pixels and transfers the accumulated charges in the second direction, and a transfer control means, which outputs, to the respective pixels and the horizontal transfer register, transfer signals for transferring charges, and the transfer control means outputs the transfer signals so that the charges generated at the pixels not belonging to the pixel set are overlapped in the first direction and accumulated in the horizontal transfer register and thereafter transferred in the second direction while the charges generated at the pixels belonging to the pixel set are accumulated in the first direction and transferred in the second direction one stage at a time.

In this case, since the transfer control means makes the charges, resulting from photoelectric conversion by the pixels not belonging to the pixel set, be accumulated in an overlapping manner, the charges that are not used as effective data can be collected together. That is, since the charges, generated by photoelectric conversion at the pixels, which do not belong to the pixel set but are positioned across a plurality of stages, can be swept out in a single transfer in the second direction, the charges generated by photoelectric conversion at the pixels belonging to the pixel set can be read out at a higher speed.

Preferably, the transfer control means outputs the transfer signals to the pixels belonging to the pixel set to make the charges generated at the pixels belonging to the pixel set be transferred in the first direction, and in the case where one stage of pixels aligned in the second direction includes pixels belonging to the pixel set, outputs the transfer signal to the horizontal transfer register at the stage prior to the transfer of the charges generated at the one stage of pixels to the horizontal transfer register.

In this case, since at the stage before the charges, which have been generated by photoelectric conversion at the pixels belonging to the pixel set, are transferred successively to the horizontal transfer register, the transfer control means outputs the transfer signal to the horizontal transfer register, the charges accumulated in the horizontal transfer register can be swept out efficiently.

Preferably, in the case where one stage of pixels aligned in the second direction includes pixels belonging to the pixel set and pixels not belonging to the pixel set, the transfer control means outputs the transfer signals to the pixels of the one stage and thereby makes the charges be transferred to the horizontal transfer register when the elements of the horizontal transfer register, which correspond to the pixels belonging to the pixel set of the one stage, have charges swept out therefrom and are enabled to receive new charges.

For example, in the case where among the pixels of the one stage, pixels that are close to the center are pixels belonging to the pixel set and pixels that are close to the respective ends are pixels not belonging to the pixel set, the transfer signals are output to the pixels of the one stage when the charges in the stage prior to this one stage have been swept out successively so that the elements of the horizontal transfer register corresponding to the pixels close to the center of the one stage are enabled to receive new charges. In this case, although the charges generated by photoelectric conversion at the pixels close to the respective ends are overlapped with the charges at the other stages, since the charges resulting from photoelectric conversion by the pixels close to the respective ends are charges that are not used as effective detection signals, the actual influence thereof will be extremely small. The charges generated by photoelectric conversion at the pixels belonging to the pixel set can thus be read out at a higher speed.

Preferably, the detector has first charge accumulating elements, accumulating charges generated at the respective pixels and transferring the accumulated charges in the first direction, and second charge accumulating elements, receiving and accumulating charges transferred in the first direction from the first charge accumulating elements and transferring the accumulated charges in the second direction, the transfer control means outputs, to the first charge accumulating elements and the second charge accumulating elements, transfer signals for transfer of charges, and in the case where one stage of pixels aligned in the second direction includes pixels belonging to the pixel set and pixels not belonging to the pixel set, the transfer control means outputs the transfer signals to the first charge accumulating elements corresponding to the pixels of the one stage and thereby makes the charges be transferred to the second charge accumulating elements when the second charge accumulating elements, which correspond to the pixels belonging to the pixel set of the one stage, have charges swept out therefrom and are enabled to receive new charges.

In this case, since the transfer control means makes the charges, resulting from photoelectric conversion by the pixels not belonging to the pixel set, be accumulated in an overlapping manner, the charges that are not used as effective data can be collected together. Since the charges, generated by photoelectric conversion at the pixels, which do not belong to the pixel set but are positioned across a plurality of stages, can be swept out in a single transfer in the second direction, the charges generated by photoelectric conversion at the pixels belonging to the pixel set can be read out at a higher speed. Also, for example, in the case where, among the pixels of the one stage, pixels that are close to the center are pixels belonging to the pixel set and pixels that are close to the respective ends are pixels not belonging to the pixel set, transfer signals are output to the first charge accumulating elements corresponding to the pixels of the one stage when the charges in the stage prior to this one stage have been swept out successively so that the second charge accumulating elements corresponding to the pixels close to the center of the one stage are enabled to receive new charges. In this case, although the charges generated by photoelectric conversion at the pixels close to the respective ends are overlapped with the charges at the other stages, since the charges resulting from photoelectric conversion by the pixels close to the respective ends are charges that are not used as effective detection signals, the actual influence thereof will be extremely small. The charges generated by photoelectric conversion at the pixels belonging to the pixel set can thus be read out at a higher speed.

Preferably, the fluorescence correlation spectroscopy analyzer is equipped with an electronic shutter signal outputting means, which outputs, to the photodetection surface, an electronic shutter signal for sweeping away the charges generated by the pixels not belonging to the pixel set. In this case, when in reading the charges from the detector, horizontal transfer by the horizontal transfer register or the second charge accumulating elements does not need to be executed if the charges generated by the pixels belonging to the pixel set are not accumulated in the horizontal transfer register or the second charge accumulating elements. The charges generated by photoelectric conversion at the pixels belonging to the pixel set can thus be read at higher speed.

BRIEF DESCRIPTION OF THE DRAWINGS

FIG. 7 shows timing charts that illustrate the operation timing of the CCD camera in the reading operation illustrated in FIG. 5 and FIGS. 6A to 6D.

FIGS. 14A and 14B are diagrams for describing the operation timings of the respective CCDs during the operations described using FIGS. 10A to 10E, FIGS. 11A to 11G, and FIGS. 12A to 12G.

FIGS. 16A to 16L are diagrams for describing another example of the operations of reading detection signals from the CCD camera in the fluorescence correlation spectroscopy analyzer.

FIGS. 17A to 17K are diagrams for describing another example of the operations of reading detection signals from the CCD camera in the fluorescence correlation spectroscopy analyzer.

BEST MODES FOR CARRYING OUT THE INVENTION

Figure 1:
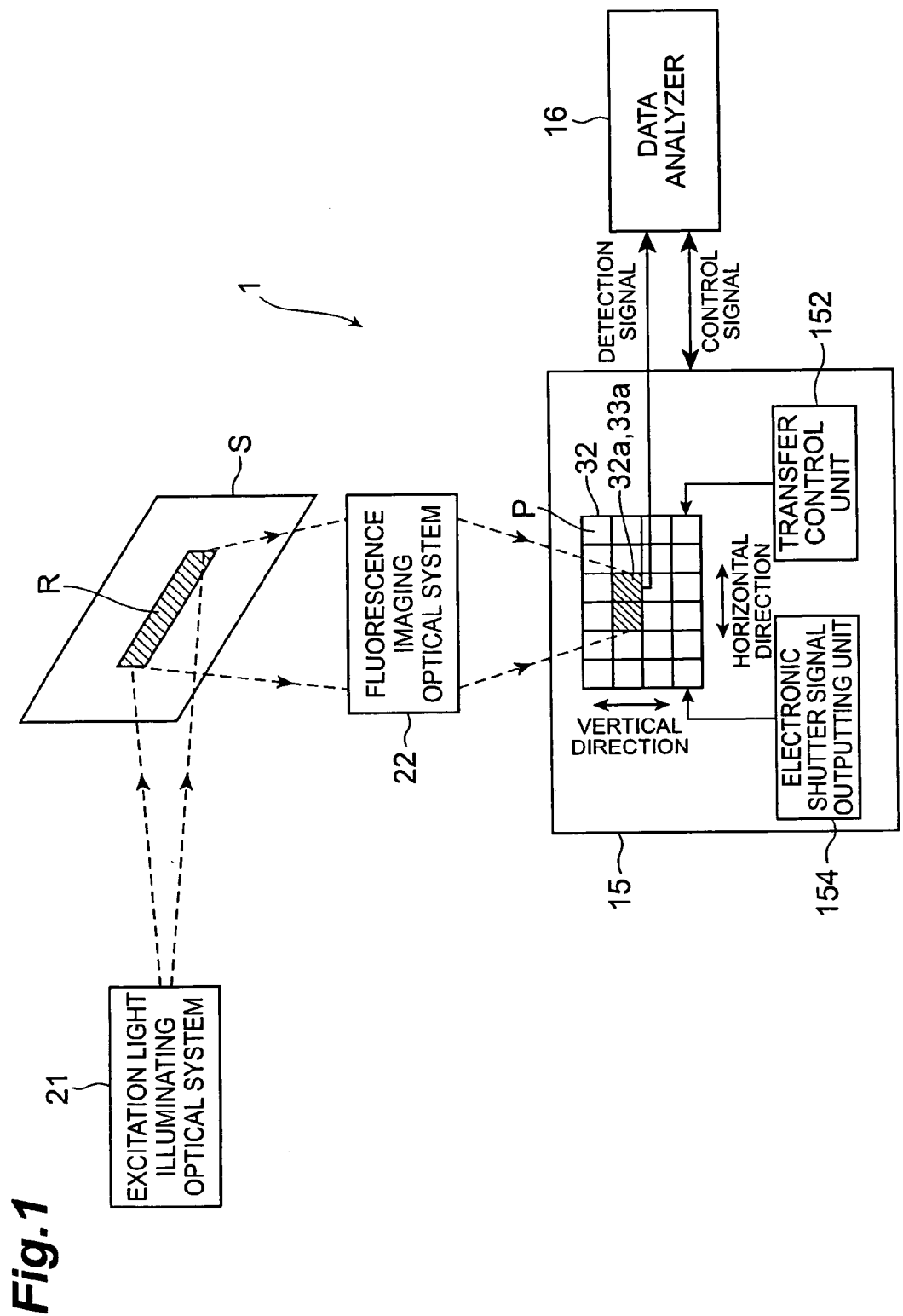
FIG. 1 is an arrangement diagram showing an embodiment of a fluorescence correlation spectroscopy analyzer.

Preferred embodiments of the present invention's fluorescence correlation spectroscopy analyzer shall now be described in detail along with the drawings. In the description of the drawings, the same elements shall be provided with the same symbols and redundant description shall be omitted. The dimensional proportions in the drawings do not necessarily match those of the description.

FIG. 1 is an arrangement diagram showing an embodiment of the present invention's fluorescence correlation spectroscopy analyzer. The fluorescence correlation spectroscopy analyzer 1 illuminates excitation light onto a measured sample, detects the fluorescence emitted from fluorescent molecules in the measured sample due to the illumination of the excitation light, and determines autocorrelation functions of the fluorescence fluctuations based on the detection signals to analyze translational diffusion motions, etc., of the fluorescent molecules. The fluorescence correlation spectroscopy analyzer 1 is equipped with an excitation light illuminating optical system 21, a fluorescence imaging optical system 22, a CCD camera 15 (detector), and a data analyzer 16 (analyzing unit).

The excitation light illuminating optical system 21 has a light source, which outputs excitation light, and a light guiding optical system, which guides the excitation light output from the light source, and is positioned so that its optical axis is directed toward the measured sample S. The excitation light illuminating optical system 21 illuminates the excitation light onto a predetermined region R of the measured sample S. A region R, onto which this excitation light is illuminated, is selected so as to contain a region of the measured sample S on which fluorescence correlation spectroscopy analysis is desired to be carried out.

The fluorescence imaging optical system 22 is positioned with its optical axis directed toward the measured sample S and forms an image of the fluorescence that is emitted from the fluorescent molecules in the region of the measured sample S onto which the excitation light has been illuminated. The fluorescence imaging optical system 22 may be positioned so that its optical axis is parallel to the optical axis of the excitation light illuminating optical system 21 or so that its optical axis forms a predetermined angle with the optical axis of the excitation light illuminating optical system 21.

The CCD camera 15 is connected to the fluorescence imaging optical system 22. The CCD camera 15 has a photodetection surface 32, a transfer control unit 152, and an electronic shutter signal outputting unit 154. The CCD camera 15 is positioned so that its photodetection surface 32 is set at the image plane position of the fluorescence that is imaged by the excitation light illuminating optical system 21. On the photodetection surface 32, a plurality of pixels P are arrayed two-dimensionally along a vertical direction (first direction) and a horizontal direction (second direction). The CCD camera 15 photoelectrically converts, according to the respective pixels P, the fluorescence made incident on photodetection surface 32, guides the charges, generated by the photoelectric conversion, to an output terminal by transferring the charges in the vertical direction and the horizontal direction, and outputs the charges guided to the output terminal as detection signals from the output terminal.

The region of photodetection surface 32 onto which the fluorescence imaged by the fluorescence imaging optical system 22 is made incident is indicated by slanted lines in the figure. This region is the fluorescence incidence region 32a. The set of pixels, comprised of pixels selected in accordance with the fluorescence incidence region 32a, is the analyzed pixel set 33a. Here, the analyzed pixel set 33a is selected so that the region thereof matches the fluorescence incidence region 32a. The analyzed pixel set 33a is arranged from a plurality of pixels that occupy a portion of all of the pixels arrayed on the photodetection surface 32.

The transfer control unit 152 is a transfer control means that outputs, to the respective pixels P of the photodetection surface 32 and to a horizontal transfer register (not shown), transfer signals for transferring charges. The electronic shutter signal outputting unit 154 is an electronic shutter signal outputting means that outputs an electronic shutter signal to the photodetection surface 32 for sweeping away the charges generated by pixels not belonging to the analyzed pixel set 33a. The provision of the electronic shutter signal outputting unit 154 is not essential.

The data analyzer 16 is connected to the CCD camera 15. The data analyzer 16 inputs the detection signals that are based on the charges generated by photoelectric conversion at the pixels belonging to the analyzed pixel set 33a among pixels P arrayed on the photodetection surface 32 of the CCD camera 15 and computes autocorrelation functions, respectively, for the input detection signals. The data analyzer 16 analyzes, as necessary, the diffusion motions of the fluorescence molecules of the measured sample S based on the computed autocorrelation functions.

In order to process the detection signals input from the CCD camera 15 in a manner associated with pixels P corresponding to the respective detection signals, the data analyzer 16 inputs information concerning transfer control by the transfer control unit 152 of the CCD camera 15. Furthermore, the data analyzer 16 selects the pixels making up the analyzed pixel set 33a in accordance with the fluorescence incidence region 32a of the photodetection surface 32. The data analyzer 16 provides, to the transfer control unit 152 and the electronic shutter signal outputting unit 154 of the CCD camera 15, instructions concerning the respective transfer control and instructions concerning the output of the electronic shutter signal as necessary. The data analyzer 16 comprises, for example, an image acquisition board and a computer.

With the fluorescence correlation spectroscopy analyzer 1 of the above-described arrangement, excitation light is illuminated onto a predetermined region of the measured sample S by the excitation light illuminating optical system 21. The fluorescence, emitted from the fluorescent molecules in the region of the measured sample S onto which the excitation light has been illuminated, is imaged by the fluorescence imaging optical system 22 onto the photodetection surface 32 of the CCD camera 15. The fluorescence that is made incident on the photodetection surface 32 is photoelectrically converted according to the respective pixels. The charges generated at the respective pixels by the photoelectric conversion are transferred as necessary in the vertical direction and the horizontal direction and thereafter output as detection signals from the output terminal of the CCD camera 15. The detection signals output by the CCD camera 15 are input into the data analyzer 16. At the data analyzer 16, autocorrelation functions of the input detection signals are determined and the diffusion motions of the fluorescent molecules are analyzed based on the autocorrelation functions.

The effects of the fluorescence correlation spectroscopy analyzer 1 shall now be described. With the fluorescence correlation spectroscopy analyzer 1, the fluorescence generated at multiple points inside the region of the measured sample S onto which the excitation light has been illuminated is detected by the plurality of pixels of the CCD camera 15 that correspond to these points to enable fluorescence correlation spectroscopy analysis to be performed simultaneously on the multiple points of the measured sample S. Also, by using the CCD camera 15, which is a charge transfer type two-dimensional photodetector, the fluorescence generated at the multiple points of the measured sample S can be detected by a simple device arrangement.

Furthermore, the data analyzer 16 determines the autocorrelation functions of the detection signals based on the charges generated at the pixels belonging to the analyzed pixel set 33a, which is comprised of a portion of the pixels of the entirety of pixels arrayed on the photodetection surface. Thus, with the CCD camera 15, there is not need to output the charges generated at all pixels of the photodetection surface as effective detection signals, and it is sufficient that at least the charges generated at the pixels belonging to the analyzed pixel set be output as the detection signals. Thus, with the fluorescence correlation spectroscopy analyzer 1, the time required to output the charges corresponding to a single frame from the CCD camera 15 can be reduced. The fluorescence correlation spectroscopy analysis can thus be performed at high speed on the multiple points of the measured sample S by the fluorescence correlation spectroscopy analyzer 1.

Also, with the fluorescence correlation spectroscopy analyzer 1, since the data analyzer 16 is provided, a measurer can readily know the results of fluorescence correlation spectroscopy analysis. The results of fluorescence correlation spectroscopy analysis include such information as how the fluorescent molecules in the measured sample S bind or move and how the size and number of the fluorescent molecules change accordingly at the respective positions of the measured sample S, for example.

Also, in the case where the pixels in the fluorescence incidence region of the photodetection surface and the pixels belonging to the analyzed pixel set are substantially matched, the data analyzer 16 determines the autocorrelation functions of the detection signals that are based on the charges generated at the pixels onto which is made incident the fluorescence generated at the region of the measured sample S illuminated by the excitation light. The fluorescence that is made incident on the photodetection surface of the CCD camera 15 is thus used effectively in fluorescence correlation spectroscopy analysis.

The fluorescence correlation spectroscopy analyzer 1 can be used favorably even under concentration conditions where only one or a few fluorescent molecules exist at a portion of the measured sample S corresponding to a single pixel of the photodetection surface of the CCD camera 15. In this case, if the information on fluorescence intensity is acquired at a high frame rate, the average number of molecules existing at each portion of the measured sample S corresponding to each pixel of the analyzed pixel set of the photodetection surface can be made known by the fluorescence intensity.

With the fluorescence correlation spectroscopy analyzer 1, since fluorescence correlation spectroscopy analysis of multiple points of the measured sample S can be performed simultaneously as mentioned above, and since the detection signals from the CCD camera 15 can be read at high speed, fluorescence correlation spectroscopy analysis can be performed simultaneously on a certain region of the measured sample S. The movement of substances inside a cell can thus be evaluated and several types of samples can be analyzed in vitro simultaneously. The fluorescence correlation spectroscopy analyzer 1 is thus widely applicable to the analysis of protein binding processes, drug screening, etc.

An analyzer that can perform fluorescence correlation spectroscopy analysis on multiple points of a measured sample is described in the above-mentioned Document 3 as well. However, the analyzer described in Document 3 uses a method called scanning FCS, wherein while scanning a point-like excitation light across a sample, the deflection of photoelectrons by an image unit of a photodetector is controlled to acquire an image by FCS. The analyzer described in Document 3 thus prepares a spatial image while scanning the point-like excitation light and differs in method from the fluorescence correlation spectroscopy analyzer 1, which performs spatial decomposition using the CCD camera 15 having the plurality of pixels arrayed two-dimensionally on the photodetection surface.

Also, in the case where scanning FCS is used to perform fluorescence correlation spectroscopy analysis on the entirety of a measured sample, such as a cell, the image acquisition may need to be made even higher in speed, depending on the diffusion rate of the sample. However, since in the case of scanning FCS, an image is acquired while scanning the point-like excitation light, the exposure time of one point in a single image is extremely short in comparison to that of the above-described embodiment, with which the excitation light is illuminated over the entirety of the predetermined region R of the measured sample S. Thus, with scanning FCS, the sensitivity of the photodetector becomes inadequate when the image acquisition is made high in speed.

Figure 2:
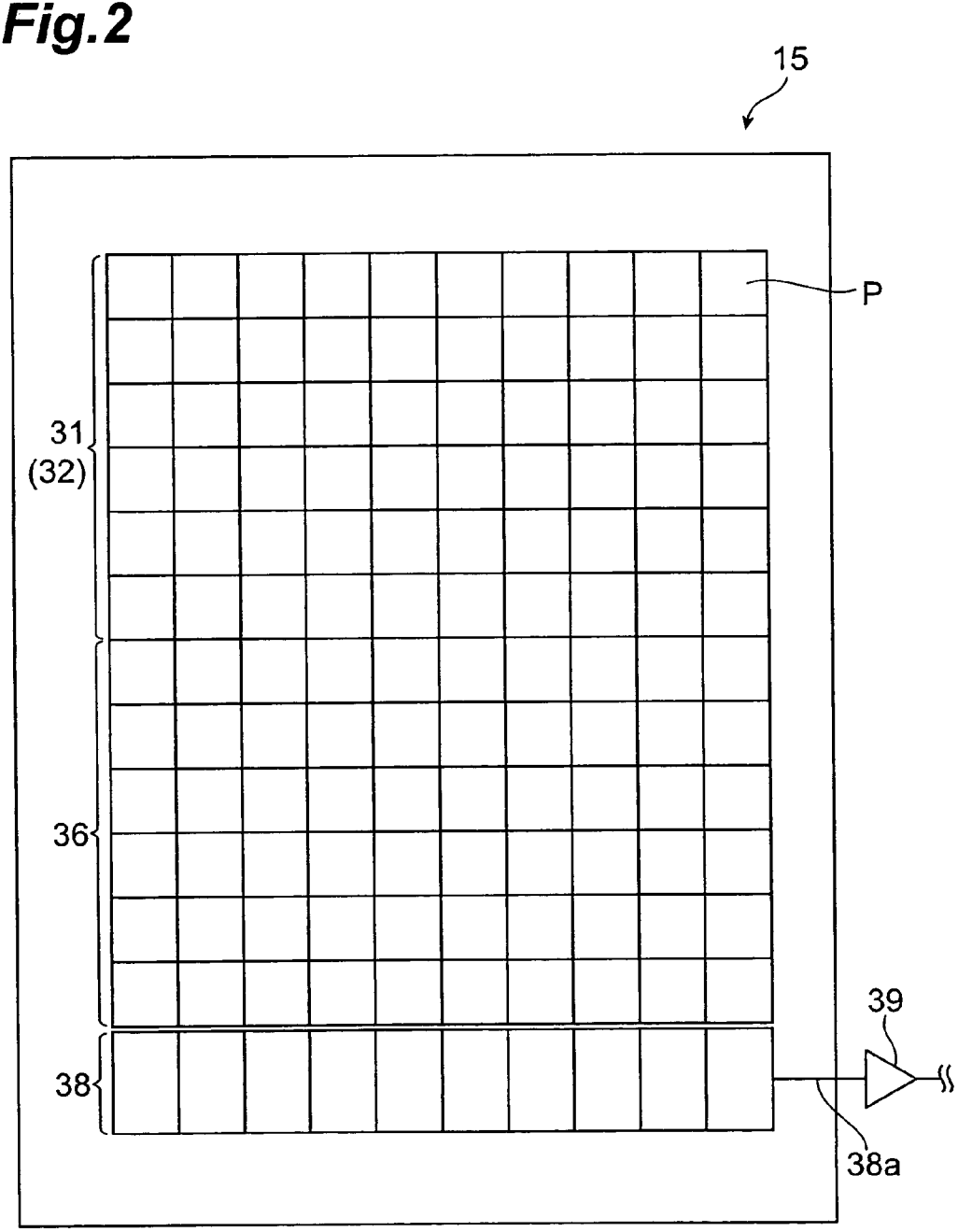
FIG. 2 is a plan view showing the CCD camera of FIG. 1 as viewed from the photodetection surface side.

The arrangement of the CCD camera 15 of FIG. 1 shall now be described with reference to FIG. 2. FIG. 2 is a plan view showing the CCD camera 15 as viewed from the photodetection surface side. However, the transfer control unit 152 and the electronic shutter signal outputting unit 154, which are shown in FIG. 1, are omitted from illustration. The CCD camera 15 is of a frame transfer type, wherein a photodetection portion 31 and an accumulation portion 36 are provided separately. The plurality of pixels P are arrayed two-dimensionally along the vertical direction (up/down direction in the figure) and the horizontal direction (left/right direction in the figure) on the surface of the CCD camera 15. Here, an example where a total of 120 pixels P are arrayed in twelve stages in the vertical direction shall be described. In each stage, ten pixels are aligned in the horizontal direction.

These pixels P are divided into pixels making up the photodetection portion 31 and pixels making up the accumulation portion 36. That is, of all of the pixels P, the 60 pixels contained in the upper half (from the first stage to the sixth stage from the top) make up the photodetection portion 31 and the 60 pixels contained in the lower half (from the seventh stage to the twelfth stage from the top) make up the accumulation portion 36. The surface of the photodetection portion 31 is the photodetection surface 32. At each pixel P that makes up the photodetection portion 31, the incident fluorescence is photoelectrically converted and the charges generated by the photoelectric conversion are transferred one stage at a time in the vertical direction. The charges that are transferred in the vertical direction from the pixels of the lowermost stage of the photodetection portion 31 are transferred to the pixels of the uppermost stage of the accumulation portion 36. At each pixel making up the accumulation portion 36, the charges received from the photodetection portion 31 are transferred one stage at a time in the vertical direction.

Also, a horizontal transfer register 38 is provided adjacent the lowermost stage of the accumulation portion 36. The charges transferred in the vertical direction from the pixels of the lowermost stage of the accumulation portion 36 are transferred to the horizontal transfer register 38. At the horizontal transfer register 38, the charges received from the accumulation portion 36 are transferred in the horizontal direction and thereby guided to an output terminal 38*a*. The charges guided to the output terminal 38*a* are output as detection signals. A reading circuit 39 is connected to the output terminal 38*a* of the horizontal transfer register 38. The detection signals output from the output terminal 38*a* of the horizontal transfer register 38 are read by the reading circuit 39.

Figure 3:
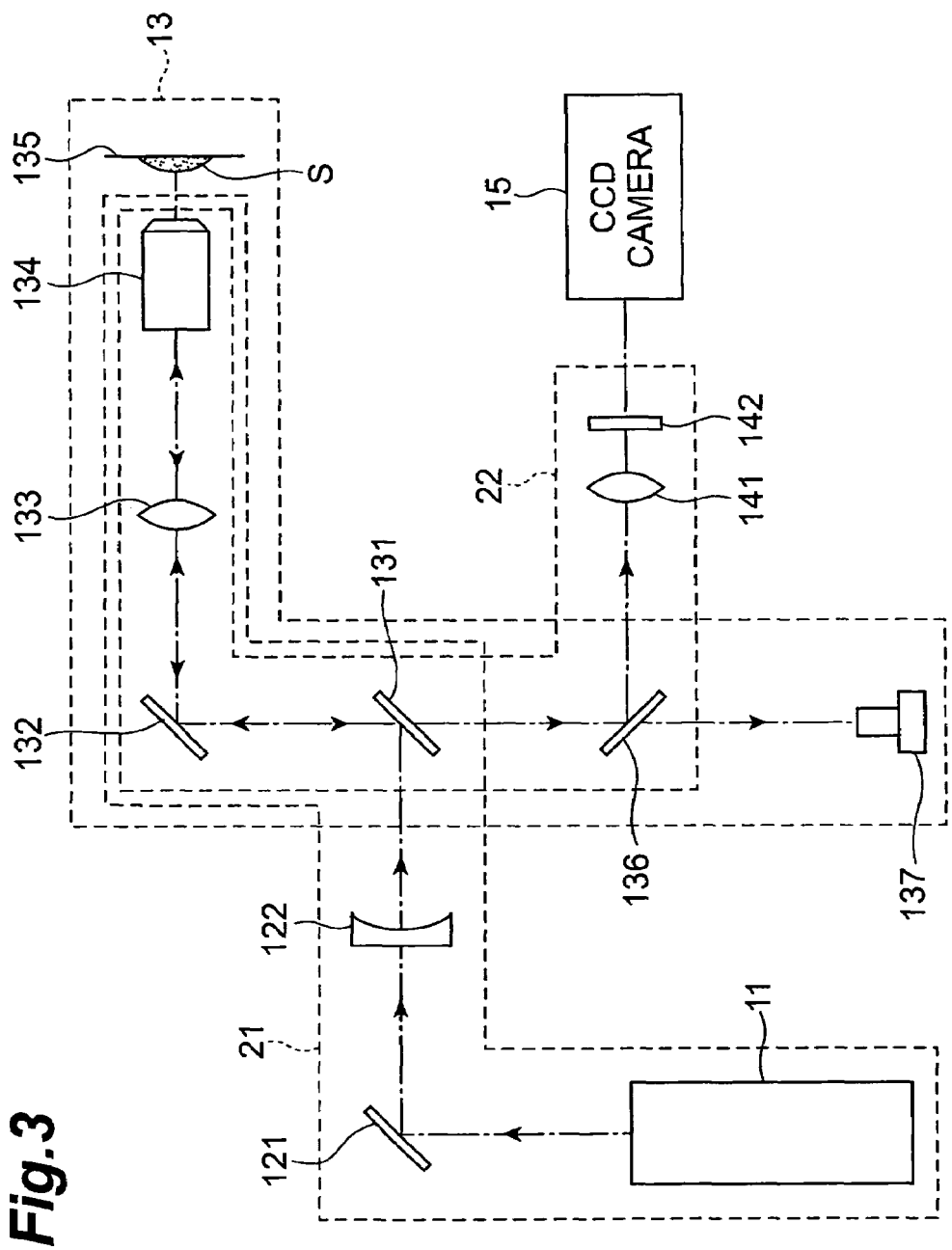
FIG. 3 is an arrangement diagram showing an example of an optical system in the fluorescence correlation spectroscopy analyzer of FIG. 1.

FIG. 3 is an arrangement diagram showing an example of an optical system in the fluorescence correlation spectroscopy analyzer 1 of FIG. 1. In FIG. 3, the CCD camera 15 is positioned so that its photodetection surface 32 is perpendicular to the optical axis direction (left/right direction in the figure) of the fluorescence that is made incident thereon. The direction perpendicular to the paper surface is the horizontal direction of the photodetection surface 32 of the CCD camera 15, and the up/down direction in the figure is the vertical direction of the photodetection surface 32. In the excitation light illuminating optical system 21, equipped in the fluorescence correlation spectroscopy analyzer 1, a laser light source 11, a mirror 121, a cylindrical lens 122, a dichroic mirror 131, a galvanomirror 132, a lens 133, and an objective lens 134 are disposed in that order along the optical path toward the measured sample S.

The laser light source 11 outputs laser light (excitation light) for exciting the fluorescent molecules in the measured sample S. The laser light source 11 is preferably a CW laser light source. As a CW laser light source, for example, an Ar laser of a wavelength of 488 nm may be used.

The mirror 121 is disposed at a position onto which the excitation light output from the laser light source 11 is made incident charges guided to the output terminal 38*a* are output as detection signals. A reading circuit 39 is connected to the output terminal 38*a* of the horizontal transfer register 38. The detection signals output from the output terminal 38*a* of the horizontal transfer register 38 are read by the reading circuit 39.

FIG. 3 is an arrangement diagram showing an example of an optical system in the fluorescence correlation spectroscopy analyzer 1 of FIG. 1. In FIG. 3, the CCD camera 15 is positioned so that its photodetection surface 32 is perpendicular to the optical axis direction (left/right direction in the figure) of the fluorescence that is made incident thereon. The direction perpendicular to the paper surface is the horizontal direction of the photodetection surface 32 of the CCD camera 15, and the up/down direction in the figure is the vertical direction of the photodetection surface 32. In the excitation light illuminating optical system 21, equipped in the fluorescence correlation spectroscopy analyzer 1, a laser light source 11, a mirror 121, a cylindrical lens 122, a dichroic mirror 131, a galvanomirror 132, a lens 133, and an objective lens 134 are disposed in that order along the optical path toward the measured sample S.

The laser light source 11 outputs laser light (excitation light) for exciting the fluorescent molecules in the measured sample S. The laser light source 11 is preferably a CW laser light source. As a CW laser light source, for example, an Ar laser of a wavelength of 488 nm may be used.

The mirror 121 is disposed at a position onto which the excitation light output from the laser light source 11 is made incident. The mirror 121 reflects the incident excitation light toward the cylindrical lens 122.

The cylindrical lens 122 is disposed at a position onto which the excitation light reflected by the mirror 121 is made incident. The cylindrical lens 122 is an excitation light shaping means that shapes the incident excitation light. That is, the cylindrical lens 122 refracts the incident excitation light in just one direction to shape the cross-sectional shape in a plane perpendicular to the optical axis of the excitation light beam and emits the shaped excitation light. A rectangular shape (slit-like shape) can be cited as an example of the shape of the shaped excited light. In this case, a rectangular excitation light is illuminated onto the measured sample S. Also, the cylindrical lens 122 is positioned so that the direction of the long side of the rectangular shape corresponds to the horizontal direction of the photodetection surface 32 of the CCD camera 15.

The dichroic mirror 131 is disposed at a position onto which the excitation light emitted from the cylindrical lens 122 is made incident. The dichroic mirror 131 reflects the excitation light emitted from the cylindrical lens 122 toward the galvanomirror 132. Also, as shall be described later, the dichroic mirror 131 allows the transmission of the fluorescence reflected by the galvanomirror 132 and eliminates the excitation light that is made incident upon being reflected by the measured sample S, etc., at that point.

The galvanomirror 132 is disposed at a position onto which the excitation light reflected by the dichroic mirror 131 is made incident. The galvanomirror 132 reflects the excitation light reflected by the dichroic mirror 131 toward the lens 133. Also, the galvanomirror 132 is a scanning means that scans the excitation light one-dimensionally across the measured sample S by being driven by a driver (not shown). When for example, the excitation light is shaped to a rectangular shape by the cylindrical lens 122, the direction of scanning of the excitation light by the galvanomirror 132 is set to the direction of the short side of the rectangular shape. The above-mentioned driver is connected to the data analyzer 16 (see FIG. 1) and the driver drives the galvanomirror 132 based on instructions from the data analyzer 16.

The lens 133 is disposed at a position onto which the excitation light reflected by the galvanomirror 132 is made incident. The lens 133 guides the excitation light reflected by the galvanomirror 132 to the objective lens 134.

The objective lens 134 is disposed at a position onto which the excitation light guided by the lens 133 is made incident. The objective lens 134 illuminates the excitation light, guided and made incident by the lens 133, onto the measured sample S.

The above-mentioned dichroic mirror 131, the galvanomirror 132, the lens 133, and the objective lens 134 make up a fluorescence microscope 13. In addition to the dichroic mirror 131, the galvanomirror 132, the lens 133, and the objective lens 134, the fluorescence microscope 13 is arranged with a stage 135, a mirror 136, and an ocular lens 137. The stage 135 is for placing the measured sample S. The mirror 136 is included in the fluorescence imaging optical system 22 to be described later and is for converting the optical path of the fluorescence that is transmitted through the dichroic mirror 131. The ocular lens 137 is disposed to enable a measurer to view, as necessary, the conditions of the measured sample S illuminated by the excitation light. When the ocular lens 137 is needed, a half-mirror is used as the mirror 136 to guide a portion of the fluorescence from the measured sample S to the ocular lens 137. Or, the mirror 136 may be disposed so as to be movable and the mirror 136 may be removed from the optical path of the fluorescence when the ocular lens 137 is to be used.

The fluorescence imaging optical system 22, equipped in the fluorescence correlation spectroscopy analyzer 1, has the objective lens 134, the lens 133, the galvanomirror 132, the dichroic mirror 131, the mirror 136, a lens 141, and a sharp cut filter 142 disposed in that order along the optical path from the measured sample S to the CCD camera 15. The dichroic mirror 131, the galvanomirror 132, the lens 133, and the objective lens 134 are provided in common to the excitation light illuminating optical system 21 and the fluorescence imaging optical system 22.

The fluorescence generated at the measured sample S becomes incident on the objective lens 134, which guides the incident fluorescence to the lens 133. The lens 133 guides the fluorescence, which has been made incident upon being guided by the objective lens 134, to the galvanomirror 132. The galvanomirror 132 reflects the fluorescence, which has been made incident upon being guided by the lens 133, to the dichroic mirror 131. The dichroic mirror 131 allows the fluorescence, which has been reflected by the galvanomirror 132, to be transmitted.

The mirror 136 is disposed at a position onto which the fluorescence, transmitted from the dichroic mirror 131, is made incident. The mirror 136 reflects the fluorescence, which has been made incident upon being transmitted through the dichroic mirror 131, and thereby converts the fluorescence optical path and makes the fluorescence optical path be matched with the image pickup axis of the CCD camera 15.

The lens 141 is disposed at a position onto which the fluorescence, reflected by the mirror 136, is made incident. Lens 141 guides the fluorescence, reflected by the mirror 136, to the CCD camera 15 and images the fluorescence on the photodetection surface 32 of the CCD camera 15.

The sharp cut filter 142 is disposed in the optical path between the lens 141 and the CCD camera 15. As the sharp cut filter 142, an optical filter, having a property of transmitting the wavelength component of the fluorescence generated at the measured sample S and practically not transmitting the wavelength component of the excitation light illuminated onto the measured sample S, is used. The sharp cut filter 142 thus transmits the fluorescence that is made incident on the photodetection surface 32 of the CCD camera 15 and at the same time eliminates the excitation light that tends to be made incident on the photodetection surface 32 of the CCD camera 15 along the same optical path as the fluorescence. This excitation light is that which is reflected by the measured sample S, etc.

With the optical system of FIG. 3, the excitation light is scanned with respect to the measured sample S by means of the galvanomirror 132. Fluorescence correlation spectroscopy analysis can thereby be performed over a wide range of the measured sample S. Also, by the galvanomirror 132 being the scanning means, the excitation light can be scanned with respect to the measured sample S at an especially high precision. However, if there is not need to scan the excitation light, the galvanomirror 132 does not have to be provided. An arrangement is also possible wherein, in place of using the galvanomirror 132, the excitation light is scanned with respect to the measured sample S by movement of the stage 135 of the fluorescence microscope 13.

The galvanomirror 132 is also provided in common to the excitation light illuminating optical system 21 and the fluorescence imaging optical system 22. Thus, the excitation light illuminated onto the measured sample S and the fluorescence generated at the measured sample S are both reflected by the galvanomirror 132. Thus, even if the position of illumination of the excitation light with respect to the measured sample S is displaced by the galvanomirror 132, since this displacement is canceled out when the fluorescence is reflected by the galvanomirror 132, the position of incidence of the fluorescence onto the photodetection surface 32 of the CCD camera 15 will not be displaced. Thus, in the case where fluorescence correlation spectroscopy analysis is performed while scanning the excitation light with respect to the measured sample S, the patterns of charge transfer and reading control at the CCD camera 15 do not need to be changed, regardless of the illumination position of the excitation light on measured sample S. Thus, by the fluorescence correlation spectroscopy analyzer 1, fluorescence correlation spectroscopy analysis can be performed readily on the entirety of the measured sample S.

Also, in the case where a CW laser light source is used as the laser light source 11, the cost can be made lower in comparison to the case where a pulsed light source is used.

Figure 4B:
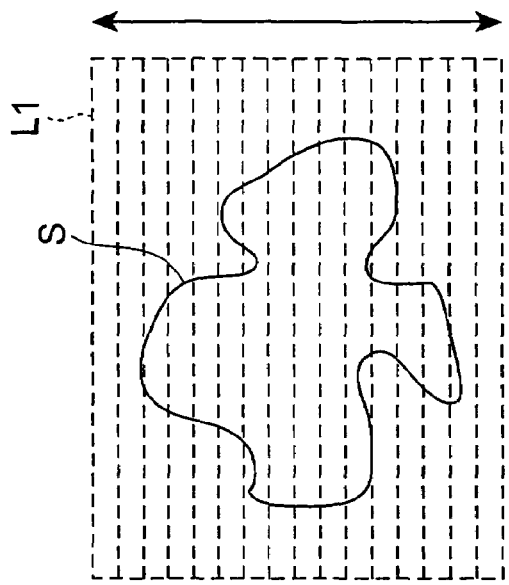
FIGS. 4A to 4D are diagrams for describing the flow of fluorescence correlation spectroscopy analysis using the fluorescence correlation spectroscopy analyzer shown in FIG. 1.
Figure 4A:
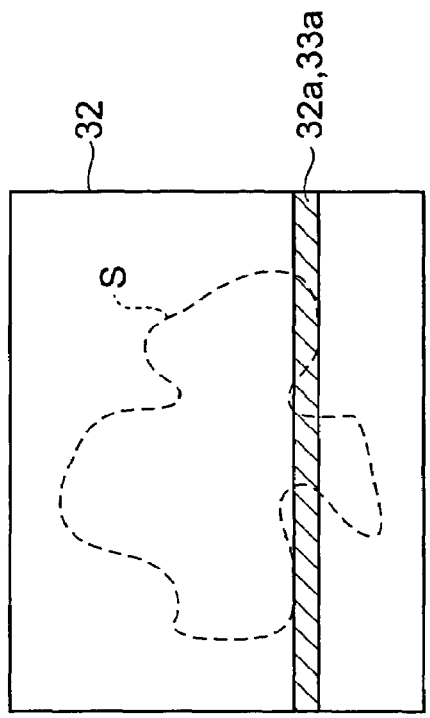

FIGS. 4A to 4D are diagrams for describing the flow of fluorescence correlation spectroscopy analysis using the fluorescence correlation spectroscopy analyzer 1 shown in FIG. 1. First, by means of the excitation light illuminating optical system 21 (see FIG. 3), the excitation light is illuminated onto the measured sample S placed on the stage 135 of the fluorescence microscope 13. Here, by shaping the excitation light to a rectangular shape by means of the cylindrical lens 122 of the excitation light illuminating optical system 21, excitation light of a rectangular shape is illuminated onto the measured sample S (FIG. 4A). In FIG. 4A, the region surrounded by dashed lines LI is the region onto which the excitation light is illuminated.

The fluorescence generated at the measured sample S onto which the excitation light is illuminated is imaged by the fluorescence imaging optical system 22 on the photodetection surface 32 of the CCD camera 15. Here, the fluorescence incidence region 32*a* is the region of the photodetection surface 32 of the CCD camera 15 onto which the fluorescence is made incident (FIG. 4B). The fluorescence incidence region 32*a* has a rectangular shape and the longitudinal direction thereof is matched to the horizontal direction (left/right direction in the figure) of the photodetection surface 32.

Figure 4D:
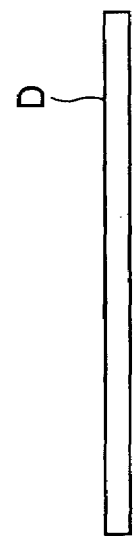
Figure 4C:
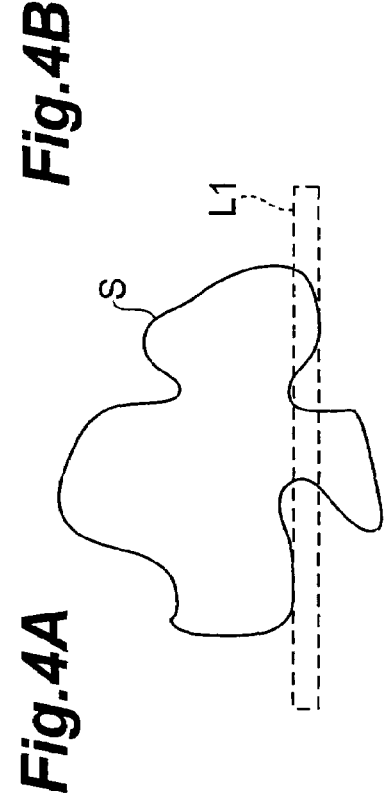

The temporal variations of the fluorescence intensities at the respective pixels in the fluorescence incidence region 32*a* are measured by driving the CCD camera 15 at a high frame rate. By then determining autocorrelation functions from these temporal variations, measurement data D can be obtained simultaneously for all of the pixels in the fluorescence incidence region 32*a* (FIG. 4C). Here, all of the pixels in the fluorescence incidence region 32*a* are selected as the pixels belonging to the analyzed pixel set 33*a*. Furthermore, by scanning the excitation light with respect to the measured sample S by means of the galvanomirror 132 (see FIG. 3), measurement data D are obtained for the entirety of the measured sample S (FIG. 4D). This scanning direction is orthogonal to the longitudinal direction of the excitation light of rectangular shape that is illuminated onto the measured sample S. Measurement data D, which are obtained by the FCS method, are, for example, the relaxation times and the y-intercepts of the autocorrelation functions. Since the relaxation times and y-intercepts reflect the sizes and numbers of the fluorescent molecules in a cell (measured sample S), information concerning at which portions of the cell the molecules are binding to each other or are moving and how the sizes and numbers of the molecules change accordingly at the respective positions of the cell are acquired for the entire cell at high speed.

Figure 5:
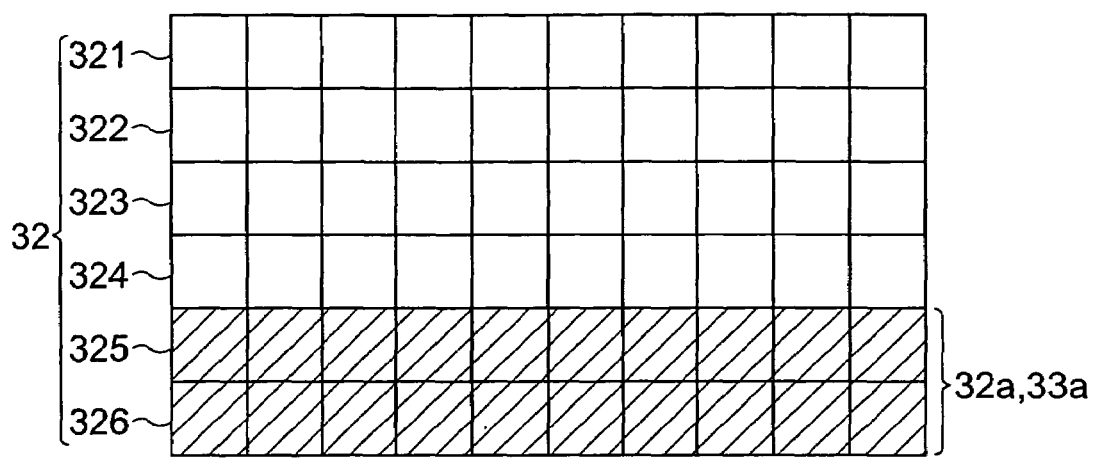
FIG. 5 is a diagram for describing an example of the operations of reading detection signals from the CCD camera in the fluorescence correlation spectroscopy analyzer.

An example of the operations of reading detection signals from the CCD camera 15 in the fluorescence correlation spectroscopy analyzer 1 shall now be described with reference to FIG. 5 and FIGS. 6A to 6D. FIG. 5 shows the photodetection surface 32 of the CCD camera 15, which is exposed to the fluorescence from the measured sample S. The photodetection surface 32 is divided into a first stage 321 to a sixth stage 326 in the vertical direction (up/down direction in the figure), and each of stages 321 to 326 has ten pixels aligned in the horizontal direction (left/right direction in the figure). The photodetection surface 32 thus has a total of 60 pixels arrayed two-dimensionally. Of these 60 pixels, the fluorescence is made incident only on the 20 pixels belonging to the fifth stage 325 and sixth stage 326. This region onto which the fluorescence is made incident is the fluorescence incidence region 32*a*. Here, the analyzed pixel set 33*a* are selected so as to be comprised of the pixels that make up the fluorescence incidence region 32*a*, that is, the 20 pixels belonging to the fifth stage 325 and sixth stage 326.

Figure 6A:
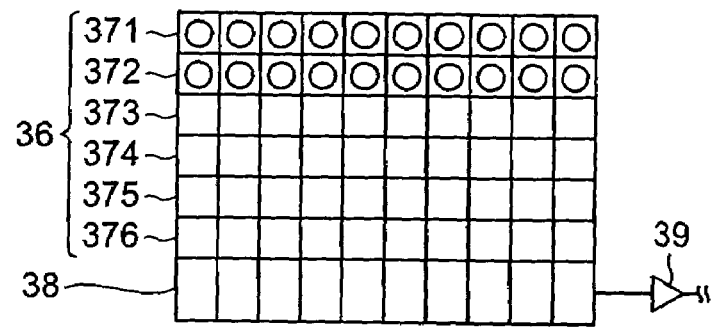
FIGS. 6A to 6D are diagrams for describing an example of the operations of reading detection signals from the CCD camera in the fluorescence correlation spectroscopy analyzer.

FIGS. 6A to 6D show the accumulation portion 36 and the horizontal transfer register 38 of the CCD camera 15. The charges generated by photoelectric conversion of the fluorescence at the respective pixels of the photodetection surface 32 in FIG. 5 are transferred one stage at a time in the vertical direction toward the accumulation portion 36. FIG. 6A shows a state immediately after the charges, generated at the respective pixels belonging to the analyzed pixel set 33*a* of the photodetection surface 32 have been transferred to the accumulation portion 36.

That is, in FIG. 6A, the charges generated at the analyzed pixel set 33*a* are accumulated in the respective pixels of a first stage 371 and a second stage 372 of the accumulation portion 36. A circle is marked in each of the pixels in which charges generated at the pixels belonging to the analyzed pixel set 33*a* are accumulated. Immediately after all of the charges generated at the analyzed pixel set 33*a* have thus been transferred to the accumulation portion 36, the electronic shutter signal is sent to the photodetection surface 32 and all of the charges generated at the pixels of photodetection surface 32 that do not belong to the analyzed pixel set 33*a* are swept away.

Figure 6B:
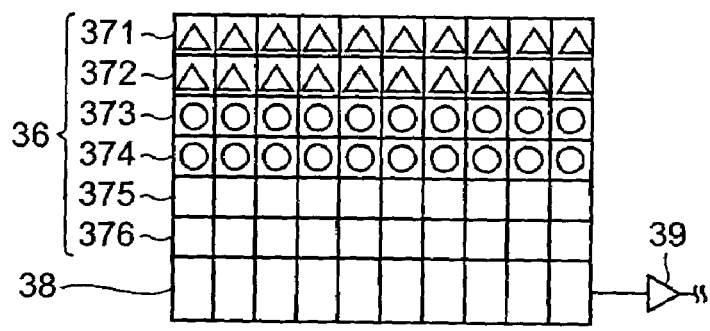

Furthermore, at the photodetection surface 32, immediately after the charges have been swept away, the next exposure is carried out, and the charges generated at the analyzed pixel set 33*a* by this exposure are transferred to the accumulation portion 36. FIG. 6B shows the state immediately after the charges, generated at the analyzed pixel set 33*a* by this exposure, have been transferred to the accumulation portion 36. At this point, the charges generated at the analyzed pixel set 33*a* by the previous exposure are transferred to a third stage 373 and a fourth stage 374. In FIG. 6B, circles are marked in the pixels in which are accumulated the charges generated by the previous exposure (shall be referred to as the "first exposure") and triangles are marked in the pixels in which are accumulated the charges generated by the present exposure (shall be referred to as the "second exposure").

Figure 6C:
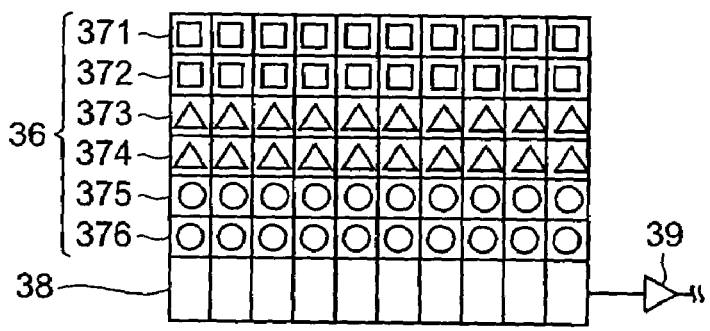

The above operations are repeated, and after the charges generated at the analyzed pixel set 33*a* have been successively accumulated in all of the first stage 371 to a sixth stage 376 of the accumulation portion 36 as shown in FIG. 6C, these charges are transferred one stage at a time to the horizontal transfer register 38 and the charges are transferred successively by the horizontal transfer register 38 toward the reading circuit 39. Exposure of the photodetection surface 32 is carried out during this operation as well. However, the exposure time must be set to be no greater than the time required for the horizontal transfer register 38 to transfer all of the charges of a single stage.

In FIG. 6C, the charges generated by the first exposure are accumulated in a fifth stage 375 and sixth stage 376, the charges generated by the second exposure are accumulated in the third stage 373 and fourth stage 374, and the charges generated by the third exposure (indicated by the squares in the figure) are accumulated in the first stage 371 and second stage 372. Also, FIG. 6D shows the state wherein the charges, generated in the first exposure at the sixth stage 326 of the photodetection surface 32 among the analyzed pixel set 33*a*, have been transferred to the horizontal transfer register 38.

Figure 6D:
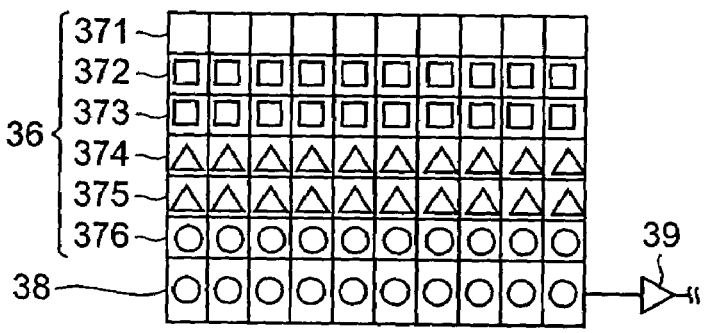

Though in FIG. 6D, charges generated by a fourth exposure are actually accumulated in the first stage 371, illustration thereof is omitted. After transferring the charges of this stage to the reading circuit 39, the horizontal transfer register 38 performs the transfer of the charges of the next stage. The reading of the detection signals of a single frame detected by the CCD camera 15 is completed by the above. Thus, in the reading operations of this example, just the charges generated by photoelectric conversion at the pixels belonging to the analyzed pixel set 33a of the photodetection surface 32 are output from the CCD camera 15 as the actual detection signals.

In the present example, by electronic shutter outputting unit 154 outputting the electronic shutter signal to the photodetection surface 32 of the CCD camera 15, the charges generated at the respective pixels not belonging to the analyzed pixel set 33a are swept away. Just the charges generated at the analyzed pixel set 33a (the pixels belonging to the fifth stage 325 and sixth stage 326 in FIG. 5) can thus be transferred repeatedly to the accumulation portion. Also, since the transfer by the horizontal transfer register 38 is carried out even during exposure of the photodetection surface 32, data can be acquired at a high repetition rate with the time taken for the horizontal transfer register 38 to horizontally transfer the charges generated at the analyzed pixel set 33a as the minimum.

In particular, with the present example, since the analyzed pixel set 33a is set so as to include the pixels of the sixth stage 326 of the photodetection surface 32, which is adjacent to the accumulation portion 36, the fluorescence information of a single frame can be read successively without gaps from the CCD camera 15 at time intervals taken for transfer of the charges of the few lines (two lines in the present example) in the vertical direction that make up the analyzed pixel set 33a. Thus, with the fluorescence correlation spectroscopy analyzer 1, the detection signals can be read at an especially high speed.

FIG. 7 shows timing charts that illustrate the operation timing of the CCD camera 15 in the reading operation described using FIG. 5 and FIGS. 6A to 6D. The respective charts in FIG. 7 illustrate, from the top, the electronic shutter timing, the exposure timing, the charge transfer timing, and the control timing.

The electronic shutter timing is the timing at which the electronic shutter is shut, that is, the timing at which the electronic shutter signal outputting unit 154 outputs the electronic shutter signal to the photodetection surface 32 (see FIG. 5). The electronic shutter is shut immediately prior to the start of exposure. The exposure timing expresses the timing at which the respective pixels of the photodetection surface 32 are exposed. The exposure time is set, for example, to 10 μs. The charge transfer timing expresses the timing for transfer of the charges, generated at the analyzed pixel set 33a of the photodetection surface 32, to the accumulation portion 36 in the vertical direction. The charge transfer is started immediately after the end of exposure. The control timing is the timing of control from the start of exposure to the start of the next exposure.

Figure 8:
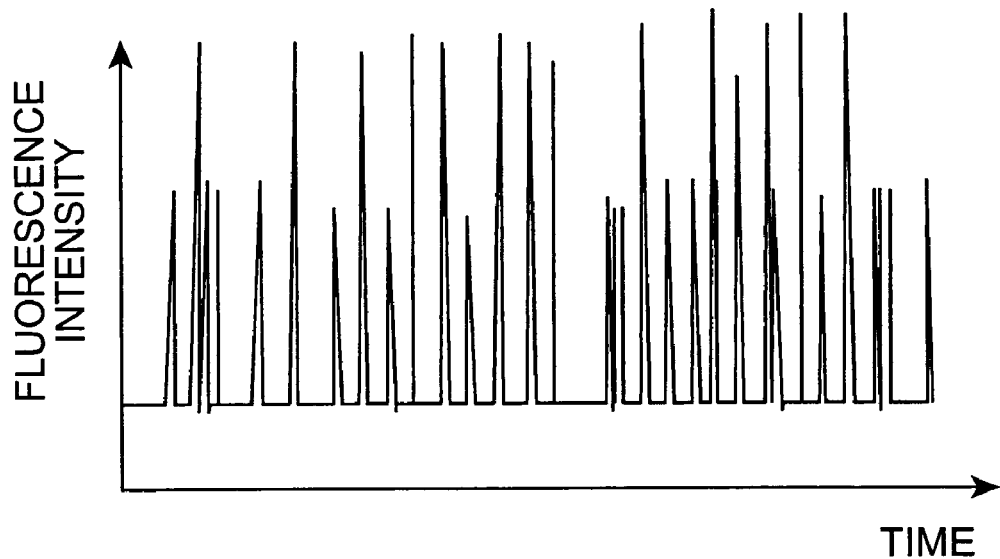
FIG. 8 is a graph showing an example of the variation in time of the fluorescence intensity detected by the CCD camera.
Figure 9:
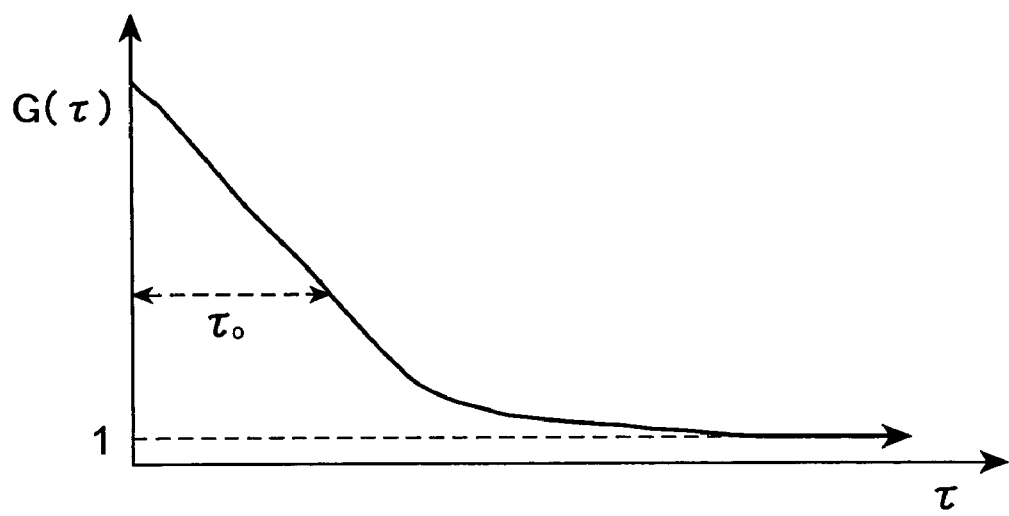
FIG. 9 is a graph showing an autocorrelation function $G(\tau)$ determined based on the graph of FIG. 8.

An example of the operations of the data analyzer 16 of FIG. 1 shall now be described using FIG. 8 and FIG. 9. FIG. 8 is a graph showing an example of the variation in time of the fluorescence intensity detected by the CCD camera 15. The ordinate of the graph expresses the fluorescence intensity and the abscissa indicates the time. Both the ordinate and abscissa are of arbitrary scales. FIG. 9 is a graph showing an autocorrelation function G(τ) determined based on the graph of FIG. 8. The ordinate of the graph expresses G(τ) and the abscissa indicates the time τ. Both the ordinate and the abscissa are of arbitrary scales. This autocorrelation function G(τ) is defined by the following equation with t being the time and I(t) being the fluorescence intensity at time t:

$$G(\tau) = \langle I(t) \cdot I(t+\tau) \rangle / \langle I(t) \rangle^2$$

In the above, $\langle I(t) \rangle$ indicates the average value of I(t).

Based on the detection signals detected by the CCD camera 15, the data analyzer 16 determines the autocorrelation function G(τ) for each pixel belonging to the analyzed pixel set 33a of the photodetection surface 32 and furthermore computes the relaxation time $\tau_0$ and the y-intercept G(0) from each autocorrelation function G(τ). Since the relaxation time $\tau_0$ and the y-intercept G(0) are functions of the size and number, respectively, of fluorescent molecules, the size and number of fluorescent molecules can be determined from the relaxation time $\tau_0$ and the y-intercept G(0). Here, the relaxation time $\tau_0$ is defined as the τ for which G(τ)=(½)G(0). With the data analyzer 16, information concerning at which portions of a cell (measured sample S) molecules are binding with each other or are moving and how the sizes and numbers of molecules are changing accordingly can be acquired for the entire cell in a short time based on the autocorrelation functions G(τ).

FIGS. 10A to 10E are diagrams for describing a modification example of the fluorescence correlation spectroscopy analyzer 1 of FIG. 1. In this modification example, the method of control of the CCD camera 15 by the transfer control unit 152 differs from that of the fluorescence correlation spectroscopy analyzer 1 of FIG. 1. Besides this, the arrangement is the same as that of the fluorescence correlation spectroscopy analyzer 1 of FIG. 1.

Figure 10A:
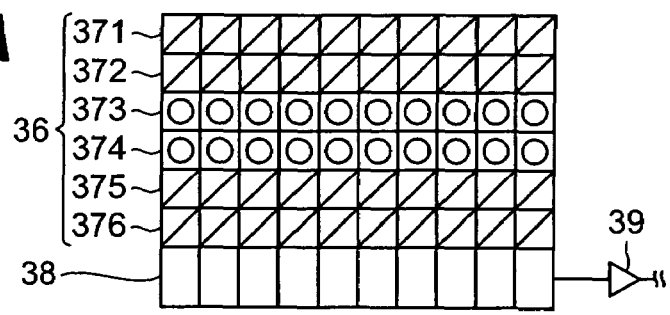
FIGS. 10A to 10E are diagrams for describing a modification example of the fluorescence correlation spectroscopy analyzer of FIG. 1.

FIG. 10A shows the state after the charges that have been generated in the respective pixels in the photodetection surface 32 of the CCD camera 15 have been transferred to the corresponding pixels of the accumulation portion 36. With the present modification example, unlike the case illustrated in FIG. 6A, an electronic shutter signal is not output by the electronic shutter signal outputting unit 154 to the pixels not belonging to the analyzed pixel set 33a of the photodetection surface 32. The charges accumulated in the pixels belonging to the first stage 371, the second stage 372, the fifth stage 375, and the sixth stage 376, which correspond to the pixels not belonging to the analyzed pixel set 33a, are thus not necessarily 0. In the figure, the pixels in which the charges generated at the pixels belonging to the analyzed pixel set 33a are accumulated are indicated by circles, and the pixels in which the charges generated at pixels not belonging to the analyzed pixel set 33a are indicated by single slanted lines.

Figure 10B:
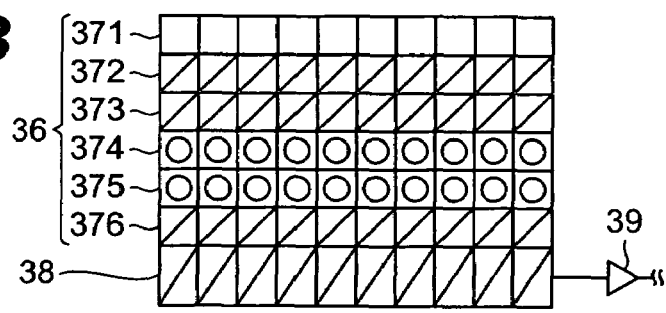

From the state of FIG. 10A, a transfer signal is input from the transfer control unit 152 into each pixel of the accumulation portion 36. The charges of the respective pixels of the accumulation portion 36 are transferred one stage at a time in the direction of the horizontal transfer register 38. The charges accumulated in the pixels of the sixth stage 376 of the accumulation portion 36 are thus transferred to the horizontal transfer register 38 as shown in FIG. 10B.

Figure 10C:
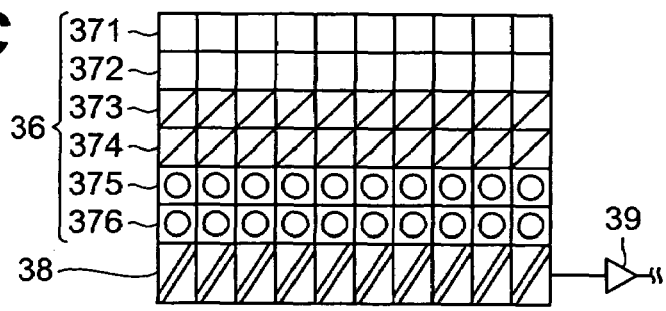

When the transfer signals are input into the accumulation portion 36 from the transfer control unit 152 again, the charges that were accumulated in the pixels of the fifth stage 375 in FIG. 10A are also transferred to the horizontal transfer register 38. Thus, in FIG. 10C, the charges that were accumulated in the pixels of the fifth stage 375 and sixth stage 376 in FIG. 10A are overlapped in the horizontal transfer register 38. In FIG. 10C, double slanted lines are indicated in the respective regions of the horizontal transfer register 38 to indicate that the charges of two stages are overlapped.

Figure 10D:
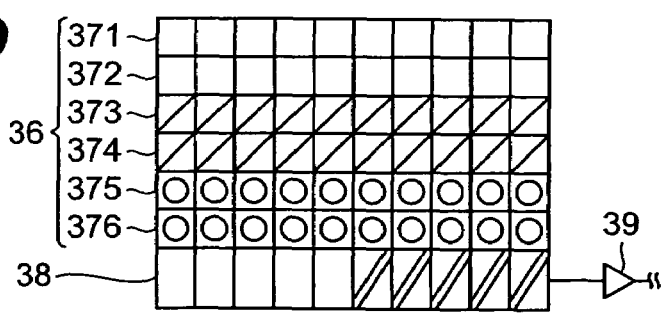
Figure 10E:
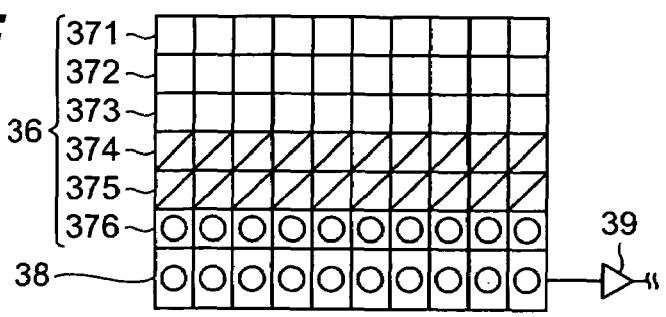

From the state of FIG. 10C, the transfer signal is input from the transfer control unit 152 to horizontal transfer register 38 and the charges accumulated in the horizontal transfer register 38 are swept out successively (FIG. 10D). Here, the charges that were accumulated in the pixels of the fourth stage 374 in FIG. 10A are not transferred to the horizontal transfer register 38 from the state of FIG. 10C since the pixels of the fourth stage 374 in FIG. 10A correspond to the pixels belonging to the analyzed pixel set 33a and thus accumulate the charges to be read as detection signals. After all of the charges accumulated in the horizontal transfer register 38 have thus been swept out, the transfer signals are input from the transfer control unit 152 to the accumulation portion 36 and the charges that were accumulated in the pixels of the fourth stage 374 in FIG. 10A are transferred to the horizontal transfer register 38 (FIG. 10E). Thereafter, the transfer signal is input from the transfer control unit 152 to the horizontal transfer register 38 and the charges that were accumulated in the pixels of the fourth stage 374 in FIG. 10A are output as detection signals to the reading circuit 39.

FIGS. 11A to 11G are diagrams for describing another modification example of the fluorescence correlation spectroscopy analyzer 1 of FIG. 1. In this modification example, the method of control of the CCD camera 15 by the transfer control unit 152 differs from that of the fluorescence correlation spectroscopy analyzer 1 of FIG. 1. Also, the analyzed pixel set in photodetection surface 32 of the CCD camera 15 differs from the analyzed pixel set 33a. The analyzed pixel set is comprised of the fourth to seventh pixels from the left in the third stage 323 and fourth stage 324 (see FIG. 5) of the photodetection surface 32 (a total of eight pixels). Besides the above, the arrangement is the same as that of the fluorescence correlation spectroscopy analyzer 1 of FIG. 1.

Figure 11A:
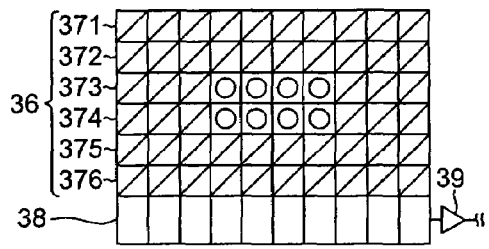
FIGS. 11A to 11G are diagrams for describing another modification example of the fluorescence correlation spectroscopy analyzer of FIG. 1.

FIG. 11A shows the state after the charges that have been generated in the respective pixels in the photodetection surface 32 of the CCD camera 15 have been transferred to the corresponding pixels of the accumulation portion 36. As with the example of FIG. 10A, with the present modification example, an electronic shutter signal is not output by the electronic shutter signal outputting unit 152 to the pixels not belonging to the analyzed pixel set of the photodetection surface 32. In the figure, the pixels in which the charges generated at the pixels belonging to the analyzed pixel set are accumulated are indicated by circles, and the pixels in which the charges generated at pixels not belonging to the analyzed pixel set are indicated by single slanted lines.

Figure 11E:
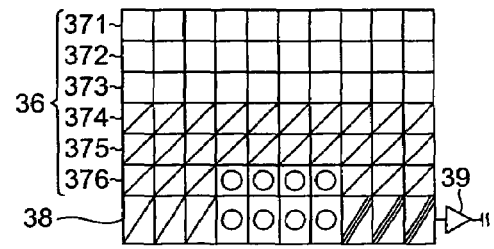
Figure 11B:
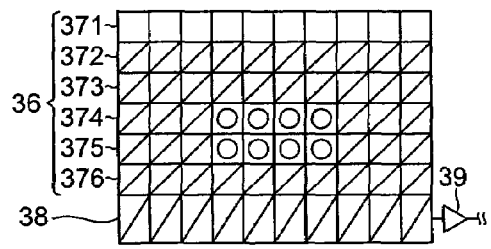
Figure 11F:
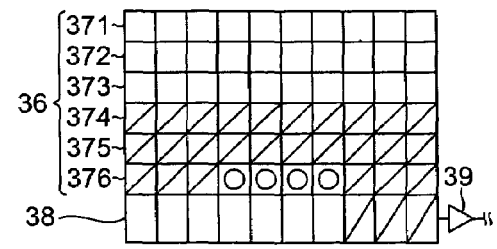
Figure 11C:
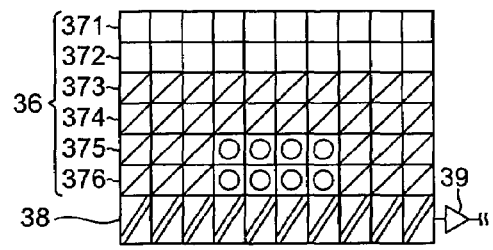

From the state of FIG. 11A, the transfer signal is input from the transfer control unit 152 into each pixel of the accumulation portion 36. The charges of the respective pixels of the accumulation portion 36 are transferred one stage at a time in the direction of the horizontal transfer register 38. The charges accumulated in the pixels of the sixth stage 376 of the accumulation portion 36 are thus transferred to the horizontal transfer register 38 as shown in FIG. 11B. When the transfer signals are input into the accumulation portion 36 from the transfer control unit 152 again, the charges that were accumulated in the pixels of the fifth stage 375 in FIG. 11A are also transferred to the horizontal transfer register 38. Thus, in FIG. 11C, the charges that were accumulated in the pixels of the fifth stage 375 and sixth stage 376 in FIG. 11A are overlapped in the horizontal transfer register 38. In FIG. 11C, double slanted lines are indicated in the respective regions of the horizontal transfer register 38 to indicate that the charges of two stages are overlapped.

Figure 11G:
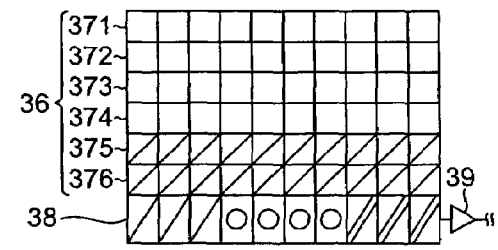
Figure 11D:
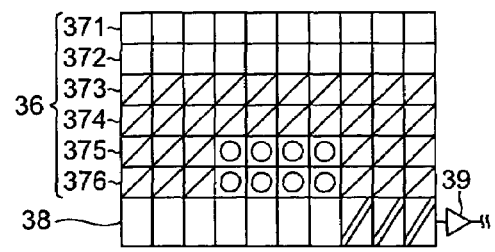

From the state of FIG. 11C, the transfer signal is input from the transfer control unit 152 to the horizontal transfer register 38 and the charges accumulated in the horizontal transfer register 38 are swept out successively. When as shown in FIG. 11D, the charges accumulated in the horizontal transfer register 38 are swept out successively and the charges of the charge accumulating elements of the horizontal transfer register 38 corresponding to the pixels of the fourth stage 374 that were provided with circles in FIG. 11A are swept out and these charge accumulating elements become able to accept new charges, the transfer signals are output from the transfer control unit 152 to the accumulation portion 36. Thus, as shown in FIG. 11E, the charges that were accumulated in the pixels of the fourth stage 374 that were provided with circles in FIG. 11A are transferred to the horizontal transfer register 38 without becoming overlapped with other charges. At the charge accumulating elements at the reading circuit side of the charge accumulating elements that receive the charges, which were accumulated in the pixels of the fourth stage 374 that were provided with circles in FIG. 11A, the charges that were accumulated in the pixels of the fourth stage 374, fifth stage 375, and sixth stage 376 in FIG. 11A are accumulated overlappingly.

At the point at which the state of FIG. 11E is attained, the transfer signal is output from the transfer control unit 152 to the horizontal transfer register 38 and the charges accumulated in the horizontal transfer-register 38 are swept out successively. When as shown in FIG. 11F, the charges accumulated in the horizontal transfer register 38 are swept out successively and the charges of the charge accumulating elements of the horizontal transfer register 38 corresponding to the pixels of the third stage 373 that were provided with circles in FIG. 11A are swept out and these charge accumulating elements become able to accept new charges, the transfer signals are output from the transfer control unit 152 to the accumulation portion 36. Thus, as shown in FIG. 11G, the charges that were accumulated in the pixels of the third stage 373 that were provided with circles in FIG. 11A are transferred to the horizontal transfer register 38 without becoming overlapped with other charges.

FIGS. 12A to 12G are diagrams for describing another modification example of the fluorescence correlation spectroscopy analyzer 1 of FIG. 1. This modification example differs from the fluorescence correlation spectroscopy analyzer 1 of FIG. 1, which uses a frame transfer type CCD camera 15, in that an interline type CCD image pickup element is used.

The CCD image pickup element of this modification example is provided with a photodetection surface 42 and a horizontal transfer register 48 (second charge accumulating elements). Photodetection surface 42 is divided into a first stage 421 to a sixth stage 426 in the vertical direction and in each of stages 421 to 426, ten photodiodes (pixels) 44a are aligned in the horizontal direction. Adjacently to the right side in the figure of each pixel is disposed a vertical transfer CCD (first charge accumulating element) 44b. The analyzed pixel set of this modification example is comprised of the fourth to seventh pixels from the left of a third stage 423 and a fourth stage 324. Here, it shall be deemed that fluorescence is incident on all of the pixels belonging to the analyzed pixel set. Also, the horizontal transfer register 48 is provided adjacent the sixth stage 426 of the photodetection surface 42.

Figure 12A:
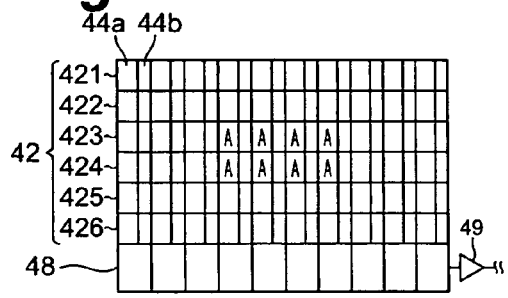
FIGS. 12A to 12G are diagrams for describing another modification example of the fluorescence correlation spectroscopy analyzer of FIG. 1.

FIG. 12A schematically illustrates a state wherein the fluorescence from the measured sample S is made incident on the photodetection surface 42. In FIG. 12A, symbols "A" are provided, respectively, in the pixels in which the charges generated at the pixels belonging to analyzed pixel set 43a are accumulated. When in the state of FIG. 12A, the transfer pulse signals are output from the transfer control unit 152 to the photodetection surface 42, the charges generated by photoelectric conversion at the respective pixels in the analyzed pixel set are output to the vertical transfer CCDs 44b and the state of FIG. 12B is attained. Since the respective pixels are put in states enabling exposure once the charges resulting from photoelectric conversion have been output, fluorescence can be detected at the same portions as those in FIG. 12A as shown in FIG. 12C. In order to distinguish from the charges detected in FIG. 12A, symbols "B" are provided in the pixels in which are accumulated the charges generated by the photoelectric conversion of the fluorescence made incident anew in FIG. 12C.

While fluorescence is thus being detected anew, the charges ("A") output to the vertical transfer CCDs 44b in FIG. 12B are transferred in the direction of the horizontal transfer register 48. At the point at which the charges have been transferred from the vertical transfer CCDs 44b corresponding to the regions provided with the symbols "B" and the receiving of new charges are enabled, the transfer pulse signals are output from the transfer control unit 152 to the photodetection surface 42 and the state shown in FIG. 12D is entered.

Figure 12E:
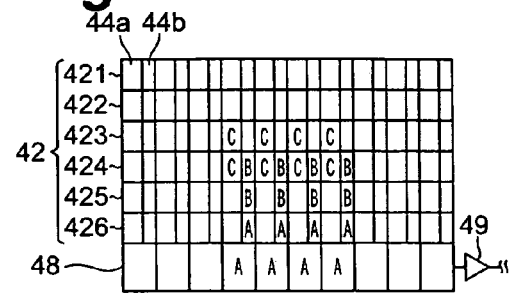
Figure 12B:
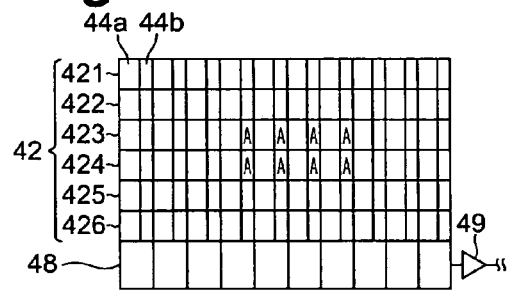
Figure 12F:
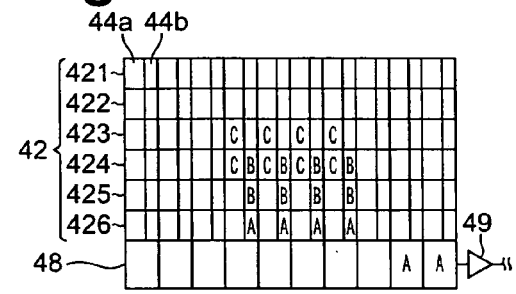
Figure 12C:
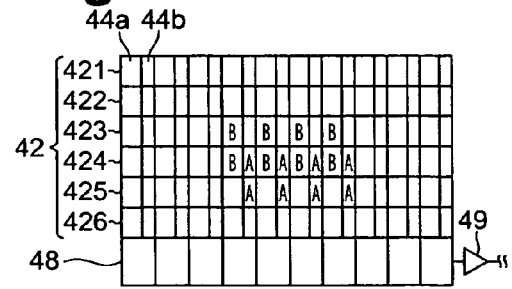

Since the respective pixels are put in states enabling exposure once the charges resulting from photoelectric conversion have been output, as shown in FIG. 12E, fluorescence can be detected at the same portions as those in FIGS. 12A and 12C. In order to distinguish from the charges detected in FIGS. 12A and 12C, symbols "C" are provided in the pixels in which are accumulated the charges generated by the photoelectric conversion of the fluorescence made incident anew in FIG. 12E. While fluorescence is thus being detected anew, the charges ("A" and "B") output to the vertical transfer CCDs 44b are transferred in the direction of the horizontal transfer register 48 and the charges ("A") resulting from the photoelectric conversion at the fourth stage 424 of FIG. 12A are transferred to the horizontal transfer register 48.

Figure 12G:
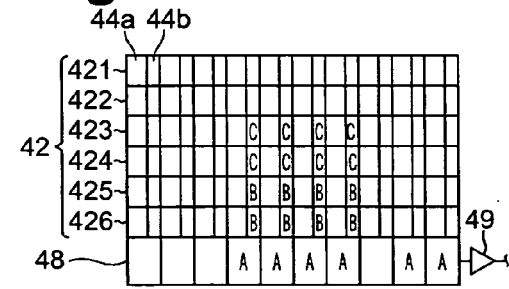
Figure 12D:
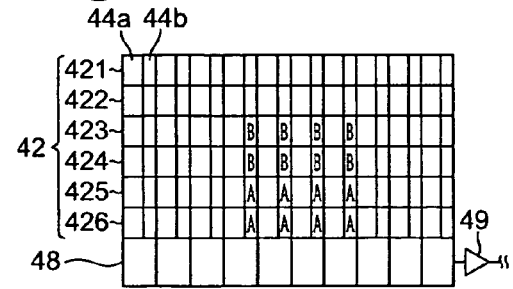

The charges ("A") transferred to the horizontal transfer register 48 are transferred in the direction of reading circuit 49 and the state of FIG. 12F is entered. When as shown in FIG. 12F, the charges accumulated in the horizontal transfer register 48 have been swept out successively and the charges ("A") of the fourth stage 424 in FIG. 12A have been swept out and the corresponding charge accumulating elements become able to accept new charges, the transfer signals are output from the transfer control unit 152 to the photodetection surface 42. Thus, as shown in FIG. 12G, the charges resulting from the photoelectric conversion at the pixels of the third stage 423 provided with the symbols "A" in FIG. 12A are transferred to the horizontal transfer register 48 without becoming overlapped with other charges.

Figure 13A:
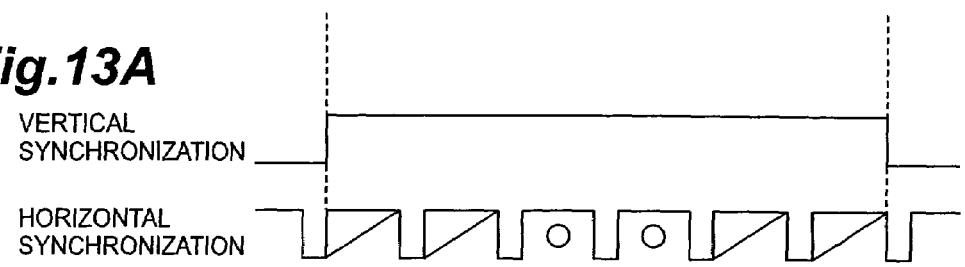
FIGS. 13A to 13D are diagrams for describing the effects of the modification examples described using FIGS. 10A to 10E, FIGS. 11A to 11G and FIGS. 12A to 12G.
Figure 13B:
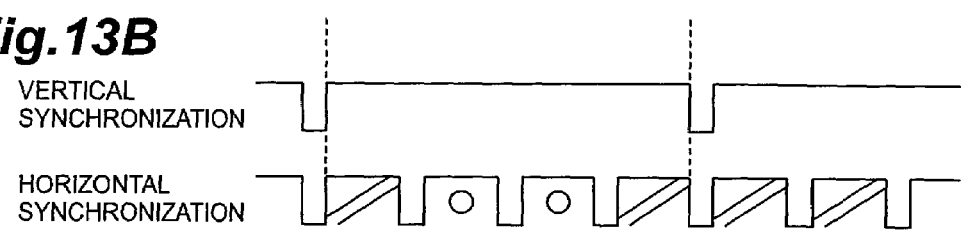

The effects of the modification examples described using FIGS. 10A to 10E, FIGS. 11A to 11G, and FIGS. 12A to 12G shall now be described with reference to FIGS. 13A to 13D. FIG. 13A shows timing charts of an arrangement of a comparative example wherein the charges generated at all pixels are output as detection signals, FIG. 13B shows timing charts for the modification example described using FIGS. 10A to 10E, FIG. 13C shows timing charts for the modification example described using FIGS. 11A to 11G, and FIG. 13D shows timing charts for the modification example described using FIGS. 12A to 12G. In the respective timing charts of FIGS. 13A to 13D, the vertical synchronization is illustrated in the upper stage and the horizontal synchronization is illustrated in the lower stage. Also, in each of the lower stages, a circle or alphabetical character indicates the transfer of charges generated at pixels belonging to the analyzed pixel set and a slanted line indicates the transfer of charges generated at pixels not belonging to the analyzed pixel set.

With the comparative example shown in FIG. 13A, since charges resulting from the photoelectric conversion by the pixels of each stage are read one stage at a time, reading in the horizontal direction must be carried out for six stages. Meanwhile, with the example shown in FIG. 13B (the modification example described using FIGS. 10A to 10E), since the charges resulting from the photoelectric conversion by the pixels not belonging to the analyzed pixel set are overlapped, even with the same horizontal direction transfer rate, the reading time of the charges of a single frame can be shortened. The detection signals can thus be read at a high speed.

Figure 13C:
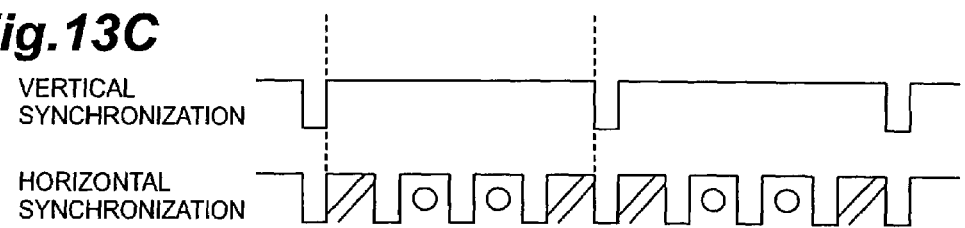

With the example shown in FIG. 13C (the modification example described using FIGS. 11A to 11G), although the pixels belonging to the third stage 323 and fourth stage 324 include both pixels belonging to the analyzed pixel set and pixels not belonging to the analyzed pixel set, even if a portion of the pixels are pixels belonging to the analyzed pixel set, the charges, resulting from photoelectric conversion by the pixels of the same stage as those pixels that do not belong to the analyzed pixel set, are read overlappingly. The reading time of the charges of a single frame can thus be shortened further. The detection signals can thus be read out at an even higher speed.

Figure 13D:
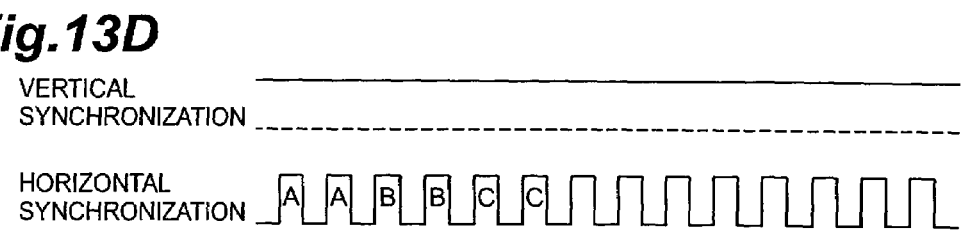

With the example shown in FIG. 13D (the modification example described using FIGS. 12A to 12G), since an interline type CCD image pickup element is used, the charges of the pixels belonging to the analyzed pixel set can be read without being influenced by the reading of the charges of the pixels not belonging to the analyzed pixel set. The detection signals can thus be read out at high speed. Also, since reading and exposure can be performed at the same time, the output data can be handled as a two-dimensional image.

The operation timings of the respective CCDs during the operations described using FIGS. 10A to 10E, FIGS. 11A to 11G, and FIGS. 12A to 12G shall now be described using FIGS. 14A, 14B, FIGS. 15A, and 15B. FIG. 14A shows timing charts for the case of performing the operations, described using FIGS. 10A to 10E or FIGS. 11A to 11G, using a frame transfer type CCD image pickup element. FIG. 14B shows timing charts for the case of performing the operations, described using FIGS. 10A to 10E or FIGS. 11A to 11G, using an interline type CCD image pickup element.

In FIGS. 14A and 14B, PIV indicates image area (photodetection portion) shift pulse signals of a frame transfer type CCD image pickup element, PSV indicates memory area (accumulation portion) shift pulse signals of the frame transfer type CCD image pickup element, PH indicates horizontal CCD shift pulse signals, SG indicates pulse signals for transfer from photodiodes to vertical transfer CCDs, PV indicates vertical shift pulse signals, and VV indicates vertical effective signals. Here, it shall be deemed that the frame transfer type CCD image pickup element has an image area of 10×6 pixels and a memory area of 10×6 pixels. Comparison of the respective vertical effective signals of FIGS. 14A and 14B shows that in cases of performing the operations described in FIGS. 10A to 10E or FIGS. 10A to 11G, reading at substantially the same speed is enabled by using either of the frame transfer type CCD image pickup element and the interline type CCD image pickup element.

Figure 15A:
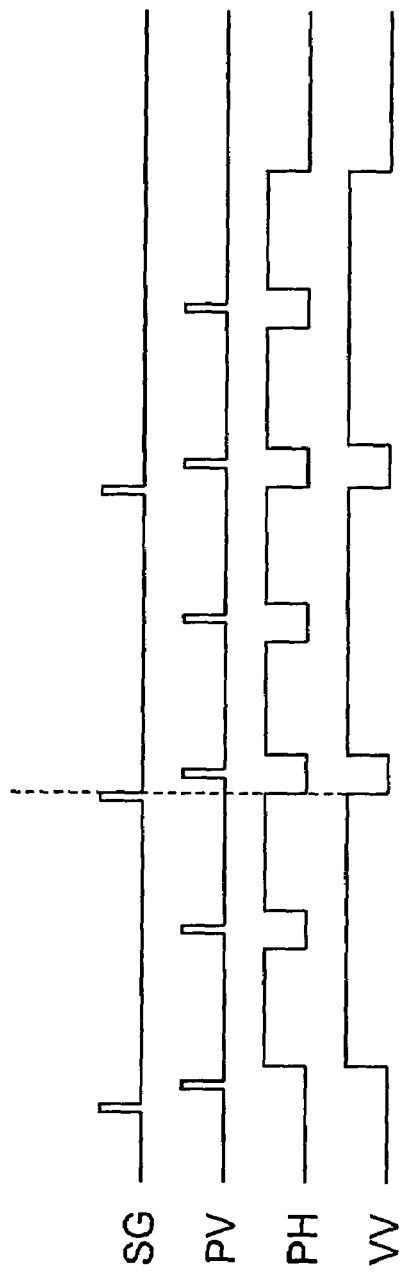
FIGS. 15A and 15B are diagrams for describing the operation timings of the respective CCDs during the operations described using FIGS. 10A to 10E, FIGS. 11A to 11G, and FIGS. 12A to 12G.
Figure 15B:
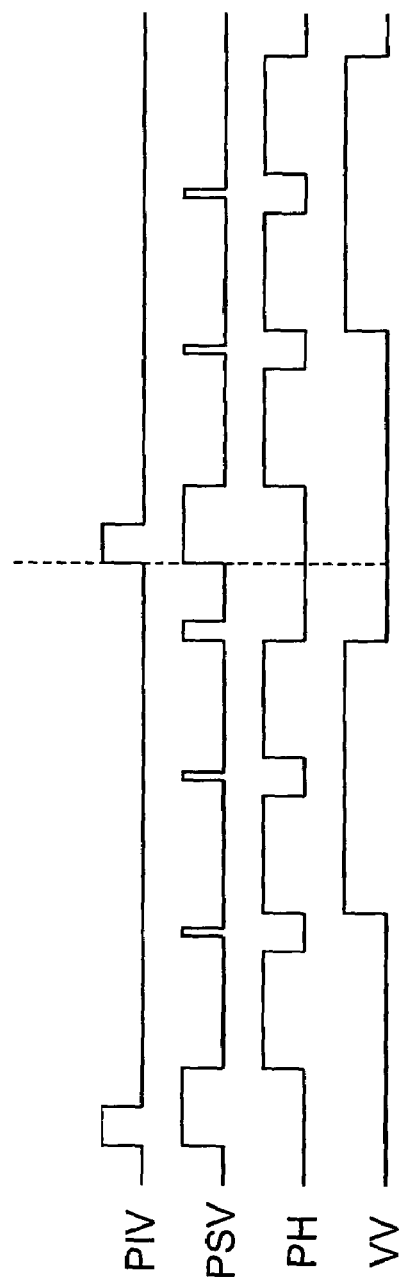

FIG. 15A shows timing charts for the case of performing the operations, described using FIGS. 12A to 12G; using an interline type CCD image pickup element. FIG. 15B shows timing charts for the case of performing the operations, described using FIGS. 12A to 12G, using a frame transfer type CCD image pickup element. The symbols used in FIGS. 15A and 15B are the same as the symbols used in FIGS. 14A and 14B. Comparison of the respective vertical effective signals of FIGS. 15A and 15B shows that when the operations described in FIGS. 12A to 12G are performed, the speed can be improved significantly when the interline type CCD image pickup element is used. This is because while the necessary areas can be added onto the unnecessary areas as they are with an interline CCD image pickup element, the same operation cannot be performed with a frame transfer type CCD image pickup element.

The present invention's fluorescence correlation spectroscopy analyzer is not limited to the above-described embodiments and various modifications are possible. For example, with the above-described embodiments, examples were described wherein the analyzed pixel set is selected so that its region matches the fluorescence incidence region. However, the analyzed pixel set may instead be selected so that a portion of the region thereof contains the fluorescence incidence region. Or, the analyzed pixel set may be selected so that the region thereof is contained in the fluorescence incidence region. Or, the analyzed pixel set may be selected so that a portion of the region thereof contains a portion of the fluorescence incidence region.

Other examples of the operations of reading detection signals from the CCD camera 15 in the fluorescence correlation spectroscopy analyzer 1 shall now be described with reference to FIGS. 16A to 16L and FIGS. 17A to 17K (see FIGS. 6A to 6D).

A method of reading charges in a case of using a frame transfer type CCD as an image pickup unit shall now be described using FIGS. 16A to 16F.

Image pickup unit 95 is of a frame transfer type having a separate photodetection portion (photodetection surface) 95a and an accumulation portion 95b. A plurality of pixels P are arrayed two-dimensionally along the vertical direction (up/down direction in the figure) and the horizontal direction (left/right direction in the figure) in image pickup unit 95. Here, an example where a total of 120 pixels P are arrayed in twelve stages in the vertical direction shall be described. In each stage, ten pixels are aligned in the horizontal direction.

These pixels P are divided into pixels making up the photodetection portion 95a and pixels making up the accumulation portion 95b. That is, of all of the pixels P, the 60 pixels contained in the upper half (from the first stage to sixth stage from the top) make up the photodetection portion and the 60 pixels contained in the lower half (from the seventh stage to twelfth stage from the top) make up the accumulation portion. At each pixel P that makes up the photodetection portion 95a, the incident fluorescence is photoelectrically converted and the charges generated by the photoelectric conversion are transferred one stage at a time in the vertical direction. The charges that are transferred in the vertical direction from the pixels of the lowermost stage (sixth stage 956) of the photodetection portion 95a are transferred to the pixels of the uppermost stage (first stage 957) of the accumulation portion 95b. At each pixel making up the accumulation portion 95b, the charges received from the photodetection portion 95a are transferred one stage at a time in the vertical direction.

Also, a horizontal transfer register 96 is provided adjacent the lowermost stage (sixth stage 962) of the accumulation portion 95b. The charges transferred in the vertical direction from the pixels of the lowermost stage (sixth stage 962) of the accumulation portion 95b are transferred to the horizontal transfer register 96. At the horizontal transfer register 96, the charges received from the accumulation portion 95b are transferred in the horizontal direction and output as detection signals.

Figure 16A:
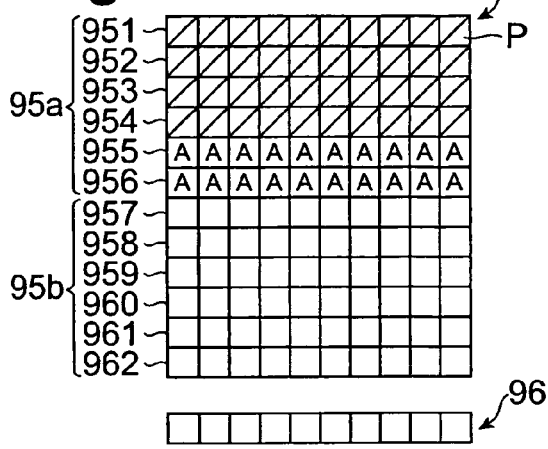
Figure 16D:
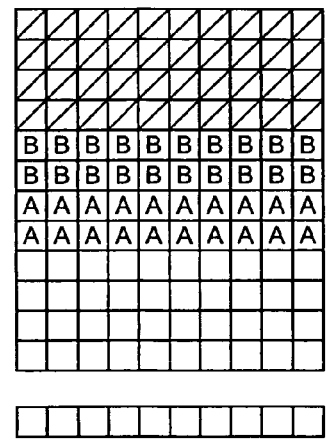
Figure 16B:
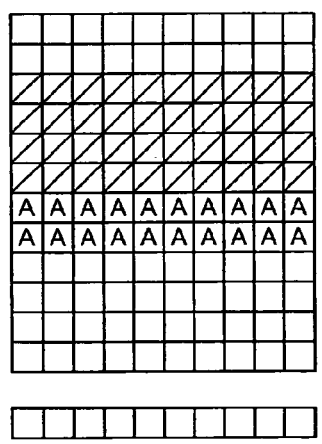

FIG. 16A schematically illustrates a state wherein fluorescence is made incident on the photodetection portion 95a and the respective pixels of photodetection portions 95a are receiving light. In FIG. 16A, it shall be deemed that the fluorescence is made incident on the region provided with the symbols "A". FIG. 16B shows the state immediately after the charges, generated at the respective pixels belonging to detection portion 95a, have been transferred to the accumulation portion 95b. That is, the charges, which were generated in accordance with the incidence of fluorescence in FIG. 16A, are accumulated in the respective pixels of a first stage 957 and a second stage 958 of the accumulation portion 95b, as shown in FIG. 16B. Immediately after all of the charges generated in accordance with the incidence of fluorescence have thus been transferred to the accumulation portion 95b, an electronic shutter signal is sent to the photodetection portion 95a and all of the charges generated at the pixels of the photodetection portion 95a onto which the fluorescence is not made incident are swept away (see FIG. 16C).

Figure 16E:
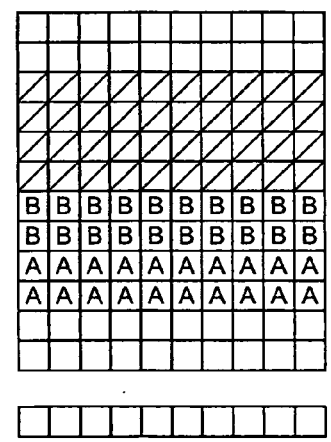

Furthermore, at the photodetection portion 95a, immediately after the charges have been swept away, the next exposure is carried out. In FIG. 16D, it shall be deemed that the fluorescence is made incident on the region provided with the symbols "B". The charges generated at the photodetection portion 95a by this exposure are transferred to the accumulation portion 95b. FIG. 16E shows the state immediately after the charges generated in accordance with the incidence of fluorescence by this exposure have been transferred to the accumulation portion 95b. At this point, the charges generated at the photodetection portion 95a by the previous exposure are transferred to a third stage 959 and a fourth stage 960.

Figure 16C:
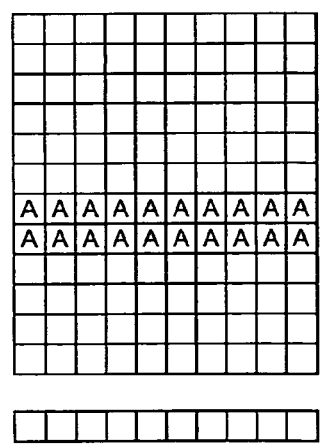
Figure 16F:
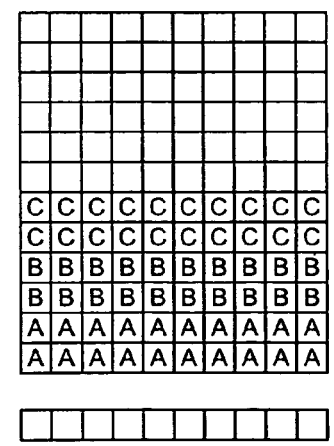

After the above operations have been repeated and the charges generated in accordance with the incidence of fluorescence have been successively accumulated in all of the first stage 957 to the sixth stage 962 of the accumulation portion 95b, these charges are transferred one stage at a time to the horizontal transfer register 96 and the charges are transferred successively by the horizontal transfer register 96 toward a reading circuit. Exposure of the photodetection surface 95a is carried out during this operation as well. However, the exposure time must be set to be no greater than the time required for the horizontal transfer register 96 to transfer all of the charges of a single stage. In FIG. 16F, the charges generated by the first exposure are accumulated in a fifth stage 961 and sixth stage 962, the charges generated by the second exposure are accumulated in the third stage 959 and fourth stage 960, and the charges generated by the third exposure (indicated by the symbols "C" in the figure) are accumulated in the first stage 957 and second stage 958. After transferring all of the charges of the first stage (lowermost stage) to the reading circuit, the horizontal transfer register 96 performs the transfer of the charges of the next stage. Thus, in the reading operations of this example, just the charges generated in accordance with the incidence of fluorescence are output as the actual detection signals.

In the present example, by a control unit (electronic shutter signal outputting means) outputting the electronic shutter signal, the charges generated at the respective pixels onto which the fluorescence is not made incident are swept away. Just the charges generated in accordance with the incidence of fluorescence can thus be transferred repeatedly to the accumulation portion. Also, since the transfer by the horizontal transfer register 96 is carried out even during exposure of the photodetection portion 95a, data can be acquired at a high repetition rate with the time taken for the horizontal transfer register 96 to horizontally transfer the charges generated in accordance with the incidence of fluorescence as the minimum. In particular, with the present example, since the region onto which the fluorescence is made incident is set so as to include the pixels of the sixth stage 95b6 of the photodetection portion 95a, which is adjacent to the accumulation portion 95b, the information of the analyzed pixel set (predetermined region) can be read successively without gaps at time intervals taken for transfer of the charges of the few lines (two lines in the present example) in the vertical direction that make up the region onto which the fluorescence is made incident. The detection signals can thus be read at an especially high speed.

Figures 16G, 16H, 16I, 16J, 16K, 16L:
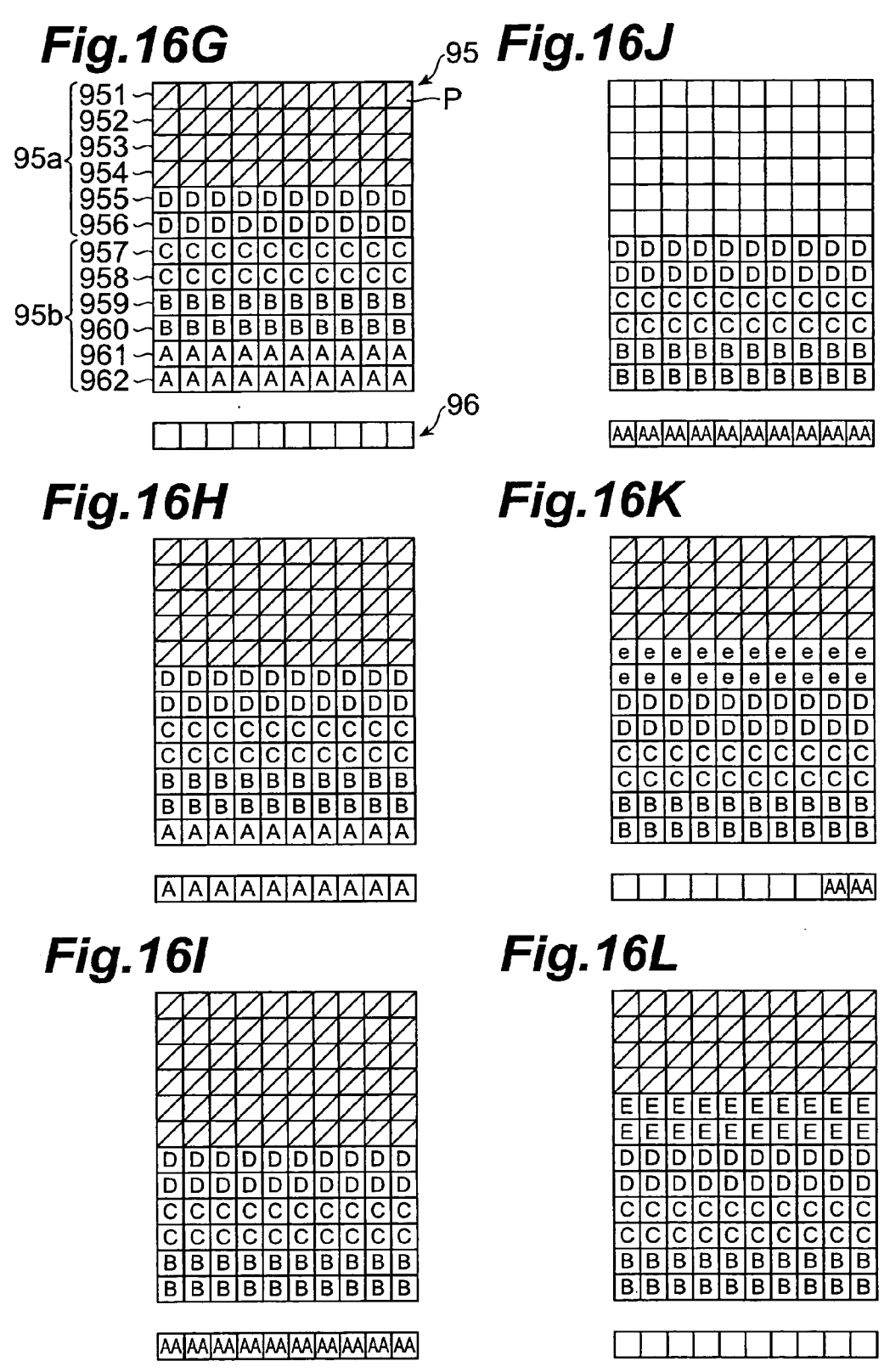

After the state of FIG. 16F, exposure and reading are carried out in the manner described next. The exposure and reading shall now be described with reference to FIGS. 16G to 16L. When further exposure is performed from the state of FIG. 16F, the state of FIG. 16G is entered. Here, all of the pixels of the accumulation portion 95b are filled with the charges that had been transferred. When vertical transfer for a single line is performed from the state of FIG. 16G, the state of FIG. 16H is entered. When vertical transfer for a single line is performed further, the state of FIG. 16I is entered. In the state shown in FIG. 16I, the charges accumulated in the first exposure (portions in the figure provided with the symbols "A") are stored in an overlapping manner in the horizontal transfer register 96 (indicated in the figure by the symbols "AA"). When the electronic shutter signal is output at this point, the charges of the pixels belonging to the photodetection portion 95a are swept away again (see FIG. 16J).

By successively reading the horizontal transfer register 96 at this point, an image can be acquired with the definition in the horizontal direction being maintained (since the charges are overlapped in the vertical direction). Furthermore, during the period of reading of the horizontal transfer register 96, the next exposure is performed (see FIG. 16K; the symbols "e" in the figure indicate a state during exposure). When the reading of the horizontal transfer register 96 is completed, the new exposure is also completed (see FIG. 16L; the symbols "E" in the figure indicate the state in which the exposure is completed). The state illustrated in FIG. 16L is equivalent to the state illustrated in FIG. 16G, and thus by repeating the exposure and reading described with reference to FIGS. 16H to 16L, images can be output continuously without unnecessarily dropping the repetition rate of image output.

Figure 17A:
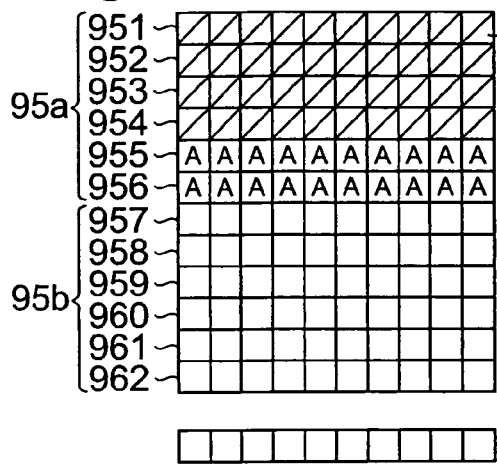
Figure 17D:
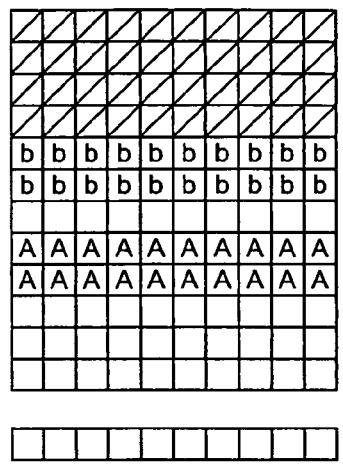
Figure 17B:
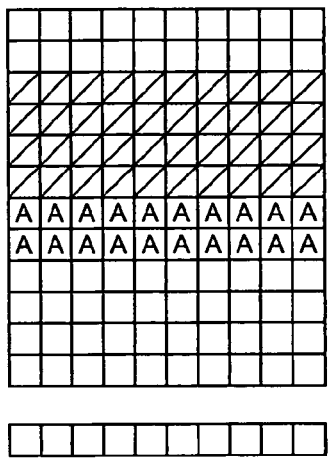
Figure 17E:
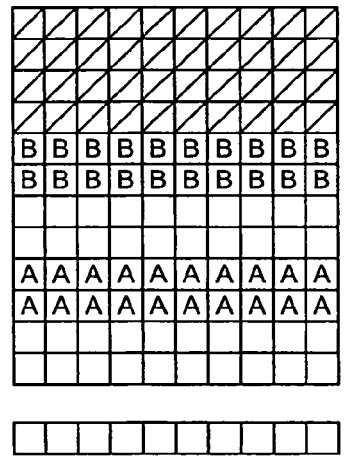
Figure 17C:
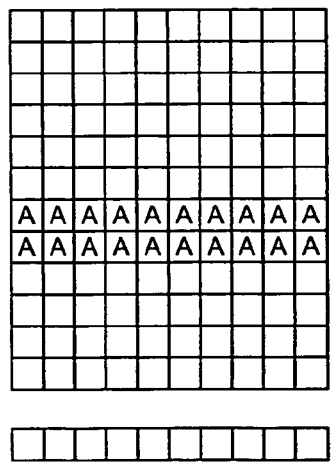

Yet another example of exposure and reading shall now be described with reference to FIGS. 17A to 17K. With FIGS. 16A to 16L, an example where overlapping in the vertical direction is performed at the horizontal reading out stage according to the analyzed pixel set was described. With FIGS. 17A to 17K, a case where overlapping in the vertical direction is not performed shall be described. In FIGS. 17A to 17C, the same exposure and transfer as those described with reference to FIGS. 16A to 16C are performed. In the case of a frame transfer type CCD, the respective driving in the vertical direction of the photodetection portion 95a and accumulation portion 95b can be performed independently of each other. Thus, from the state shown in FIG. 17C, transfer in the vertical direction is performed at the accumulation portion 95b while performing exposure at the photodetection portion 95a (indicated by the symbols "b" in the figure). When vertical transfer of two lines have been performed at the accumulation portion 95b, the exposure at the photodetection portion 95a is completed (see FIG. 17E). Driving is performed so that a gap of two lines is formed as shown in FIG. 17E because two lines are used as the analyzed pixel set. This gap is thus set based on an appropriate value that is derived from the number of lines of the accumulation portion and the vertical unit of the pixel set.

Figure 17F:
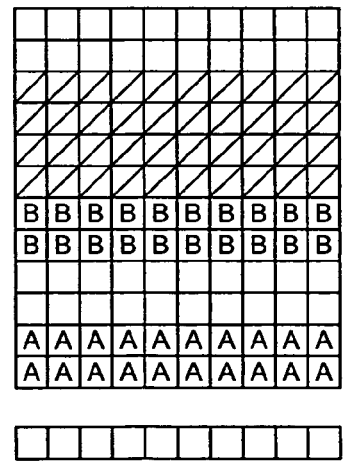
Figures 17G, 17H, 17I, 17J, 17K:
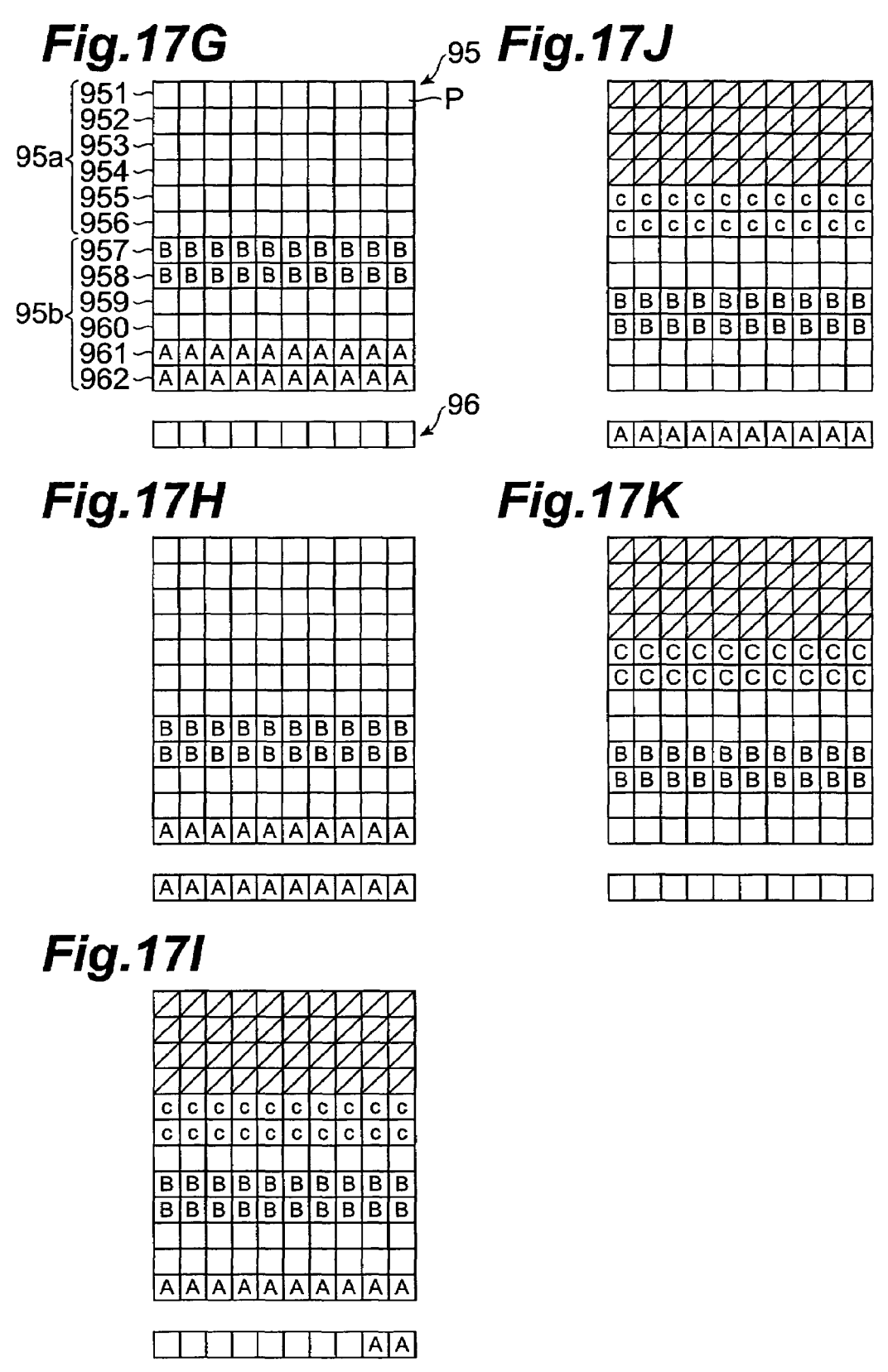

From the state of FIG. 17E, vertical transfer is performed at both photodetection portion 95a and accumulation portion 95b and the state of FIG. 17F is entered. The electronic shutter signal is output at the state shown in FIG. 17F to sweep away the charges accumulated in the photodetection portion 95a (see FIG. 17G). When from the state of FIG. 17G, further vertical transfer by one line is performed, the first line of charges, indicated by the symbols "A", is transferred to the horizontal transfer register 96, as shown in FIG. 17H. Then as shown in FIG. 17I, exposure is performed at the photodetection portion 95a while reading the horizontal transfer register 96 (the symbols "c" in the figure indicate that exposure is in progress). When the reading of the "A" charges of the first line is completed, further vertical transfer is performed just at the accumulation portion 95b to transfer the "A" charges of the next line to the horizontal transfer register 96 (see FIG. 17J). When the reading of the horizontal transfer register 96 is then completed, the exposure at the photodetection portion 95a is also completed and the state shown in FIG. 17K is entered. The state illustrated in FIG. 17K is equivalent to the state illustrated in FIG. 17E, and thus by repeating the exposure and reading described with reference to FIGS. 17F to 17K, images can be output continuously without unnecessarily dropping the repetition rate of image output.

Industrial Applicability

The present invention's fluorescence correlation spectroscopy analyzer can be used as a fluorescence correlation spectroscopy analyzer used for the analysis of protein binding processes and for drug screening, etc. In particular, with the present invention, a fluorescence correlation spectroscopy analyzer, which can perform fluorescence correlation spectroscopy analysis on multiple points of a measured sample simultaneously and at high speed, is realized.

The invention claimed is:

1. Fluorescence correlation spectroscopy analyzer comprising:

an excitation light illuminating optical system, illuminating excitation light onto a predetermined region of a measured sample;

a fluorescence imaging optical system, imaging the fluorescence emitted from fluorescent molecules within the predetermined region of the measured sample onto which the excitation light has been illuminated from the excitation light illuminating optical system;

a detector, having a photodetection surface, disposed on an image plane position of the fluorescence imaged by the fluorescence imaging optical system and provided with a plurality of pixels that are arrayed two-dimensionally along a first direction and a second direction that intersect mutually, photoelectrically converting, according to each of the pixels, the fluorescence made incident on the photodetection surface, transferring the charges generated by the photoelectrical conversion in the first direction and the second direction, and outputting the charges as detection signals corresponding to fluorescence intensities from an output terminal; and an analyzing unit, inputting the detection signals from a plurality of analyzed pixels belonging to an analyzed pixel set, comprising a portion of pixels selected from among all of the pixels, arrayed on the photodetection surface, in accordance with the incidence region of the photodetection surface on which the fluorescence is imaged by the fluorescence imaging optical system, and determining an autocorrelation function for each of the detection signals, thereby determining the autocorrelation functions of temporal variations of the fluorescence intensities for the respective analyzed pixels included in the analyzed pixel set.

2. The fluorescence correlation spectroscopy analyzer according to claim 1, wherein on the photodetection surface, the pixel set is selected so that the region thereof substantially matches the incidence region of the fluorescence.

3. The fluorescence correlation spectroscopy analyzer according to claim 1, further comprising a scanning means, by which the excitation light, illuminated by the excitation light illuminating optical system onto the predetermined region of the measured sample, is scanned with respect to the measured sample.

4. The fluorescence correlation spectroscopy analyzer according to claim 3, wherein the scanning means is a galvanomirror.

5. The fluorescence correlation spectroscopy analyzer according to claim 1, wherein the detector has a horizontal transfer register, receiving and accumulating the charges that are transferred in the first direction from the pixels and transferring the accumulated charges in the second direction, and a transfer control means, outputting, to the respective pixels and the horizontal transfer register, transfer signals for transferring charges, and the transfer control means outputs the transfer signals so that the charges generated at the pixels not belonging to the pixel set are overlapped in the first direction and accumulated in the horizontal transfer register and thereafter transferred in the second direction while the charges generated at the pixels belonging to the pixel set are accumulated in the first direction and transferred in the second direction one stage at a time.

6. The fluorescence correlation spectroscopy analyzer according to claim 5, wherein the transfer control means outputs the transfer signals to the pixels belonging to the pixel set to make the charges generated at the pixels belonging to the pixel set be transferred in the first direction, and in the case where one stage of pixels aligned in the second direction includes a pixel belonging to the pixel set, outputs the transfer signals to the horizontal transfer register at the stage prior to the transfer of the charges generated at the one stage of pixels to the horizontal transfer register.

7. The fluorescence correlation spectroscopy analyzer according to claim 5, wherein, in the case where one stage of pixels aligned in the second direction includes a pixel belonging to the pixel set and a pixel not belonging to the pixel set, the transfer control means outputs the transfer signals to the pixels of the one stage and thereby makes the charges be transferred to the horizontal transfer register when the elements of the horizontal transfer register, which correspond to the pixels belonging to the pixel set of the one stage, have charges swept out therefrom and are enabled to receive new charges.

8. The fluorescence correlation spectroscopy analyzer according to claim 1, wherein the detector has first charge accumulating elements, accumulating charges generated at the respective pixels and transferring the accumulated charges in the first direction, and second charge accumulating elements, receiving and accumulating charges transferred in the first direction from the first charge accumulating elements and transferring the accumulated charges in the second direction, the transfer control means outputs, to the first charge accumulating elements and the second charge accumulating elements, transfer signals for transfer of charges, and in the case where one stage of pixels aligned in the second direction includes a pixel belonging to the pixel set and a pixel not belonging to the pixel set, the transfer control means outputs the transfer signals to the first charge accumulating elements corresponding to the pixels of the one stage and thereby makes the charges be transferred to the second charge accumulating elements when the second charge accumulating elements, which correspond to the pixels belonging to the pixel set of the one stage, have charges swept out therefrom and are enabled to receive new charges.

9. The fluorescence correlation spectroscopy analyzer according to claim 1, further comprising an electronic shutter signal outputting means, which outputs, to the photodetection surface, an electronic shutter signal for sweeping away the charges generated by the pixels not belonging to the pixel set.

* * * * *